US 6,700,131 B2

(12) United States Patent
Nishihara et al.

(10) Patent No.: US 6,700,131 B2
(45) Date of Patent: Mar. 2, 2004

(54) SYSTEMS FOR DETECTING AND COMPENSATING FOR IMAGE ARTIFACTS WHILE SCANNING AN IMAGINE PLATE

(75) Inventors: H. Keith Nishihara, Los Altos, CA (US); Brian P. Wilfley, Los Altos, CA (US)

(73) Assignee: Alara, Inc., Hayward, CA (US)

( * ) Notice: Subject to any disclaimer, the term of this patent is extended or adjusted under 35 U.S.C. 154(b) by 0 days.

(21) Appl. No.: 09/847,950

(22) Filed: May 2, 2001

(65) Prior Publication Data

US 2003/0127611 A1 Jul. 10, 2003

Related U.S. Application Data

(60) Provisional application No. 60/201,324, filed on May 2, 2000.

(51) Int. Cl.[7] .......................... G01N 23/04; G03B 42/08
(52) U.S. Cl. ........................................ 250/586; 250/584
(58) Field of Search ................................. 250/584, 585, 250/586, 590, 458.1, 459.1, 234, 235; 356/344; 359/212

(56) References Cited

U.S. PATENT DOCUMENTS

| 4,476,873 A | 10/1984 | Sorenson et al. ............ 128/660 |
| 5,623,146 A | 4/1997 | Jones et al. ................... 250/334 |
| 5,635,728 A | 6/1997 | Cantu et al. .................. 250/584 |
| 6,201,628 B1 | 3/2001 | Basiji et al. .................. 359/212 |
| 6,355,938 B1 * | 3/2002 | Cantu et al. .................. 250/584 |
| 2003/0123613 A1 * | 7/2003 | Evans et al. .................. 378/146 |

* cited by examiner

Primary Examiner—Constantine Hannaher
Assistant Examiner—Otilia Gabor
(74) Attorney, Agent, or Firm—Heller Ehrman White & McAuliffe LLP

(57) ABSTRACT

A method of compensating for differences in detective gain between a plurality of different scanning heads in a multiple scanning head imaging plate scanner, comprising: (a) scanning each of the scanning heads across an imaging plate thereby determining the detected signal at successive locations across the imaging plate for each of the scanning heads; (b) calculating an inverse relationship to the detected signal at successive locations across the imaging plate for each of the scanning heads; (c) scanning each of the scanning heads across an imaging plate containing an image thereon, thereby determining an image value at the successive locations across the imaging plate for each of the scanning heads; and (d) applying the inverse relationship to the determined image values at the successive locations across the imaging plate for each of the scanning heads.

90 Claims, 15 Drawing Sheets

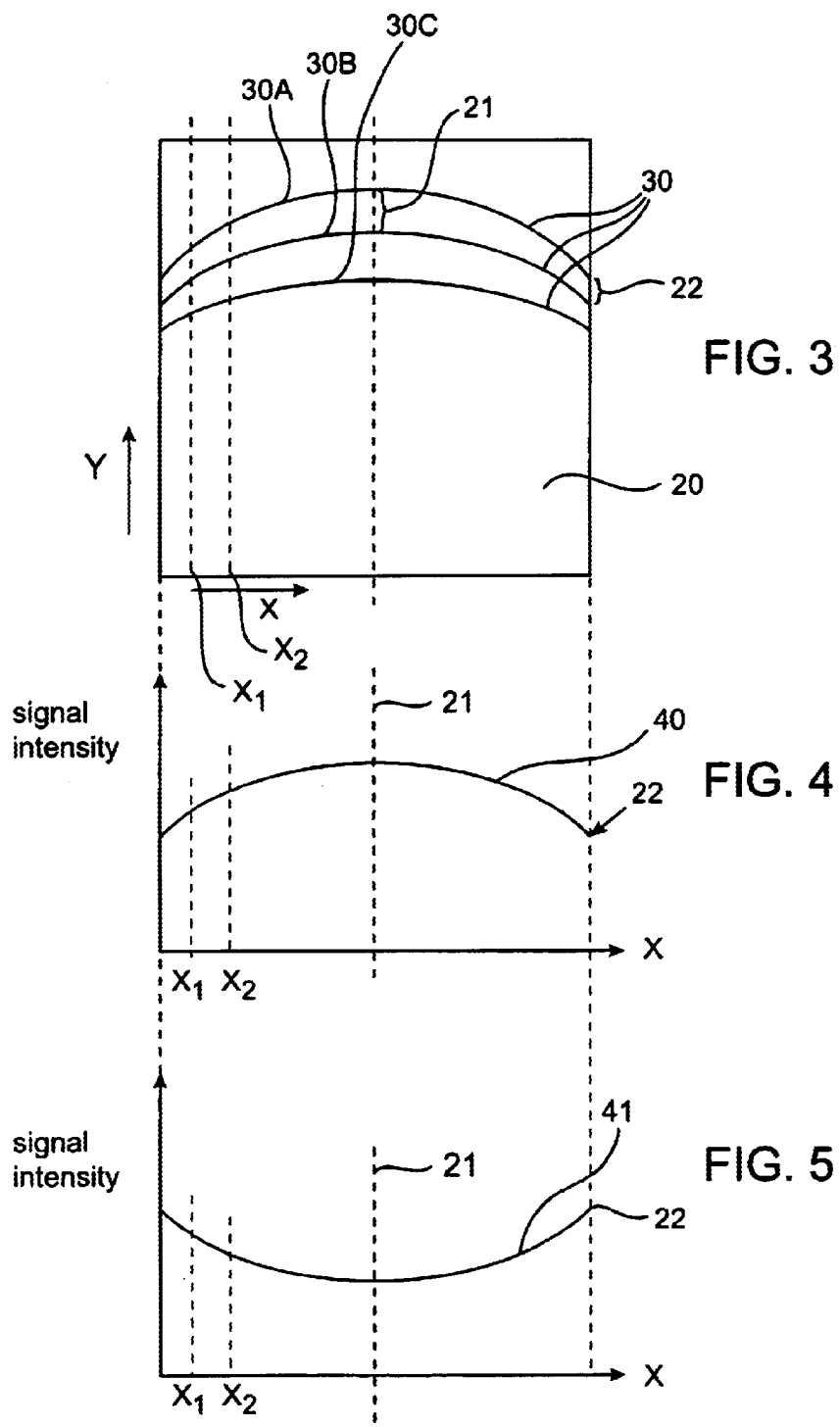

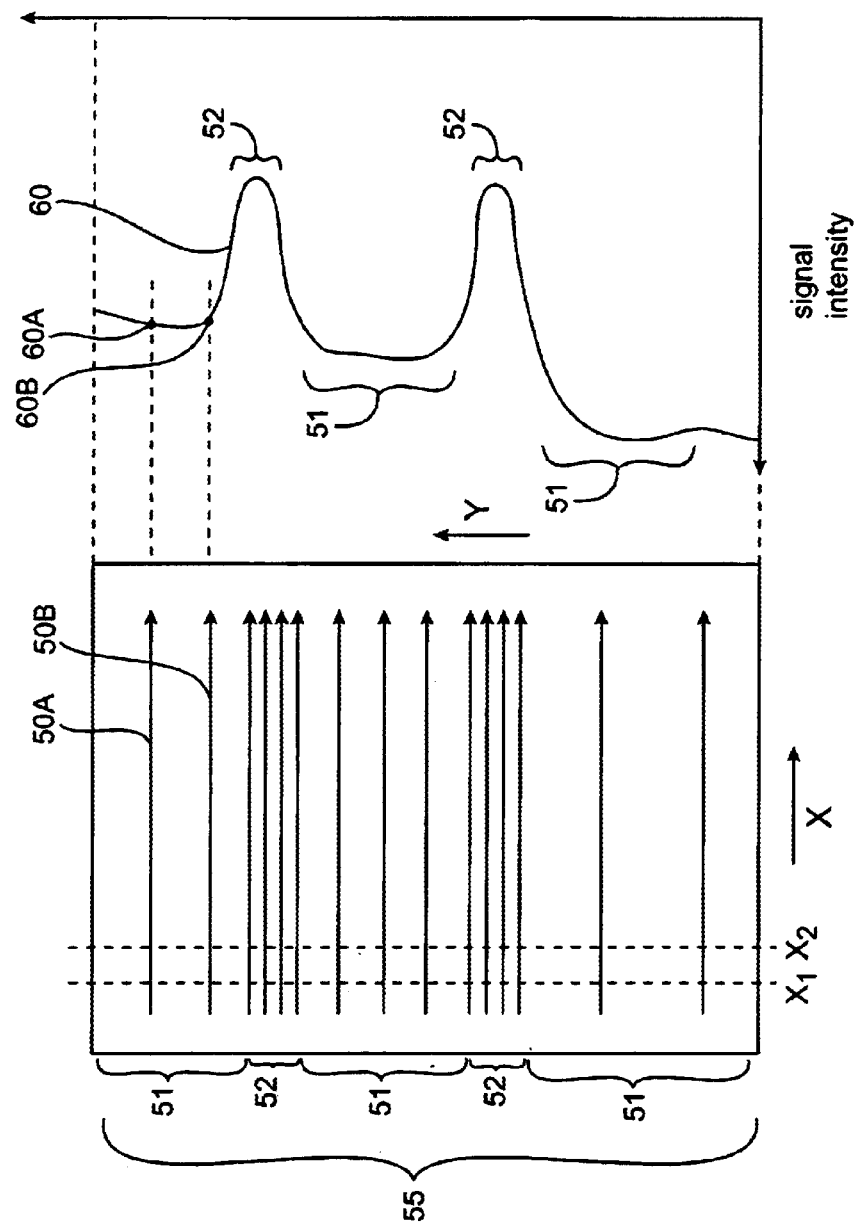

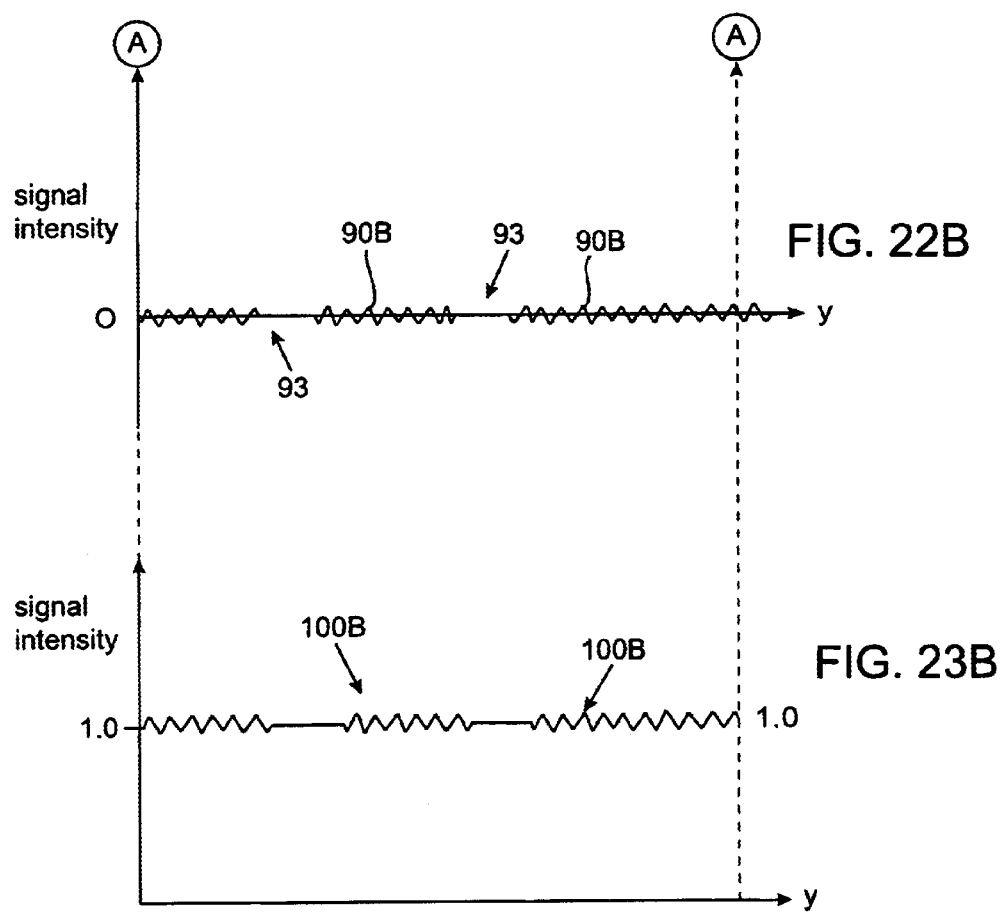

SYSTEMS FOR DETECTING AND COMPENSATING FOR IMAGE ARTIFACTS WHILE SCANNING AN IMAGINE PLATE

CROSS-REFERENCES TO RELATED APPLICATIONS

This application is a continuation of, and claims the benefit of priority from U.S. application Ser. No. 60/201,324, filed May 2, 2000, the full disclosure of which is incorporated herein by reference.

TECHNICAL FIELD

The present invention relates to scanning of imaging plates in general and to scanning of storage phosphor medical imaging plates in particular.

BACKGROUND OF THE INVENTION (a) Image Plate Scanning:

Imaging plates, such as storage phosphor imaging plates, have become standard in the field of Computed Radiography (CR) as the medium onto which an image of a portion of the patient's body can stored. The image on such a phosphor imaging plate is extracted by scanning the imaging plate with a scanner. Typically, a phosphor imaging plate is scanned by passing a scanning laser beam over the surface of the imaging plate while recording light emitted from the imaging plate in response to the laser beam. By recording the phosphorescence emission corresponding to each of the pixels of the imaging plate with a detector such as a photomultiplier, the image stored therein can be re-created (such that it can be displayed on a computer terminal).

The act of scanning an imaging plate by passing a scanning laser beam thereacross is inherently destructive (i.e.: it releases the energy stored in the phosphor screen). As such, a particular image stored on an imaging plate can only be scanned (i.e. read) once.

Unfortunately, when scanning an imaging plate to re-create the image stored therein (such that it can then be displayed on a computer terminal) image artifacts tend to appear in the final image. For example, alternating bands of lighter and darker regions, which run across the image, tend to be seen. As will be explained, such bands may be generated by uneven (i.e.: varying speed) movement of the imaging plate relative to the scanner (in what is commonly called the "slow scan direction", and referred to herein as the "Y" direction). This may be due to simple repeating mechanical irregularities in the scanner which thereby positions successive scan lines at uneven spacing along the length of the imaging plate. It may also be caused by vibrations perpendicular to the plane of the imaging plate which affect the optical focus of the scanning mechanism. In addition, various multi-head scanning systems tend to generate artifacts simply due to the fact that the different scanning heads each have their own optical paths which exhibit different optical characteristics. This is especially true in the case where each of the various scanning heads has its own dedicated laser.

Therefore, unwanted image artifacts can be divided into two broad groups. The first being those unwanted image artifacts caused by variations in the speed of movement of the scanner with respect to the imaging plate or by small vibrations either in the slow scan (i.e.: "Y") direction or normal to the imaging plate. The second being those unwanted image artifacts caused by differences between various scanning heads (when using a scanner with more than one scanning head). These two groups are discussed separately below.

(b) "Ripple" or "Banding" Artifacts:

A variety of different systems exist to scan imaging plates, such as storage phosphor imaging plates by passing one or more scanning heads over the surface of the imaging plate.

In a first existing system, a single scanning head is moved back and forth across the surface of the imaging plate while the imaging plate is moved relative to the scanner in the Y direction. Specifically, the imaging plate is moved in a direction that is perpendicular to scanner head movement such that the scanning head passes over the imaging plate along a plurality of parallel or generally parallel paths (in an "X" direction). In one type of system, a rotating or oscillating mirror directs a laser beam across the imaging plate, and the imaging plate is then advanced an incremental distance. This process is repeated such that the scanning head traces a series of parallel paths across the imaging plate. In another type of system, the imaging plate is continuously advanced as the scanning head is passed thereover, such that the scanning head traces a series of parallel paths across the imaging plate. Alternatively, the scanning head may itself be moved back and forth in the X direction across the surface of the imaging plate.

In a second existing system, the imaging plate is wrapped around a cylinder, and the cylinder is rotated while a single scanning head moves down the length of the cylinder. An example of such a system is found U.S. Pat. No. 5,635,728.

In a third system, which is novel and was developed by the present Applicants, a plurality of (typically three) scanning heads are positioned around the perimeter of a rotary scanner, and the scanner is rotated while an imaging plate is advanced thereunder. An example of such a system is found in PCT Published Application WO 00/19477. In this system, each of the scanning heads sequentially trace a curved path across the surface of the imaging plate and the movement of the imaging plate thereunder causes these curved paths to be spaced apart from one another along the length of the imaging plate. As the imaging plate is advanced under the rotating scanner, the entire surface of the plate is scanned.

Unfortunately, in all of the above described systems, any inconsistency or periodic variation in the speed of movement between the imaging plate and the scanner will result in successive scan lines (i.e.: the paths taken by the scanning head(s) across the surface of the imaging plate) being spaced unevenly apart. This unevenness between successive scan lines causes "banding" or "ripples" to occur in the final image. This is true both in the case of a linear path scanner which is kept at a fixed location with its scanning head directing a laser beam in a straight path across an imaging plate, and in the case where a plurality of scanning heads are rotating around a common center of a scanner.

As mentioned above, the scanning of an imaging plate releases the energy trapped therein. Therefore, when successive scan lines are too close together, the edges of the laser beam spot (which passes along each successive scan line) will tend to overlap such that "oversampling" of the image occurs. In other words, part of the energy representing the brightness of the image stored in a particular pixel will have already been released by the previous scan line, thereby reducing the intensity of the image when the pixel is scanned. As such, the image energy trapped within a second pixel disposed on a second scan line will have been partially released when a first (ie: previous) adjacent scan line has passed over the imaging plate. When a region of the imaging plate has been oversampled in this manner, a dark band will tend to occur which runs across the image (in a path generally parallel to the scan lines). Conversely, should the successive scan lines be positioned too far apart, the image will tend to be undersampled, resulting in a light band passing across the image.

Even a very small degree of unevenness in the scan line spacing can give rise to detectable banding artifacts in this type of scanner because the pixel intensities are preferably digitized to a high degree of precision (typically 16 or more bits per pixel).

Such alternating light and dark bands will become especially apparent when the intensities of the individual pixels in the image are scaled and presented to an operator in a final (on screen or printed) image. Such alternating banding will typically appear as thin bands in the final (on screen or printed) image such that the image appears to have "ripples" running along its length. In the case of a linear back and forth scanning head, these ripples will appear as straight lines and in the case of a rotary scanner, these ripples will appear in curved arcs.

The unevenness in the speed at which the imaging plate moves relative to the scanner is typically introduced by very small mechanical inaccuracies in the transportation system that moves the imaging plate. For example, should movement of the imaging plate be performed by a transport mechanism which comprises a worm gear, the center worm gear may itself be at least slightly off-axis. In this case, rotation of the worm gear at a constant angular speed results in a repeating pattern of variable speed changes in the movement of the imaging plate. Specifically, this pattern (which may comprise the movement of the imaging plate continually changing speed to different speeds) will repeat once for every rotation of the worm gear.

There are many alternate drive configurations that may be employed in the slow scan (i.e.: "Y-direction") transport mechanism that can give rise to small periodic velocity variations due to mechanical tolerance limitations. Examples include gear trains and pulleys. Accordingly, since several different factors may introduce speed variances at the same time, the periodic pattern of lighter and darker bands in the image may have components at different frequencies. Harmonics of a fundamental frequency may also occur due to the particular characteristics of a periodic vibration source.

Accordingly, what is desired is a system which both detects, and compensates for, repeating patterns of variations in scan line distance separation along the length of the imaging plate, such that "banding" or a "rippled" appearance of the final (on screen or printed) image can be avoided.

(c) Multiple Scanning Head Artifacts:

An important advantage of multi-head scanning systems which pass a plurality of separate scanning heads across an imaging plate is that they can increase both the speed and duty cycle of the scanning. A disadvantage of such multi-head scanning systems is that each of the scanning heads will typically have a different detective gain. Accordingly, each scanning head will read a slightly different image intensity (i.e.: detect a slightly different signal) for the same amount of actual phosphorescence emissions signal actually received therein.

Although such differences in detective gain vary among the various scanning heads (i.e.: at spaced apart scan lines in the Y-direction), such differences in detective gain may also vary among the various scanning heads depending upon the position of the scanning head across the imaging plate (i.e.: such differences in detective gain may also vary in the X-direction).

This is due to the fact that each scanning head has its own optical train, which will have its own light transmission characteristics. Furthermore, should each of the separate scanning heads/optical trains have its own dedicated laser, differences in laser output strength among the various lasers will also occur. In addition, each of the scanning heads may tend to focus their laser beams at slightly different locations. For example, in the case of a rotating multi-head scanner with a plurality of scanning heads located around its perimeter, each of the scanning heads may tend to focus its laser beam at slightly different radial distance from the center of the scanner. Accordingly, when such a scanner is rotated (at a x fixed location positioned over a constantly moving imaging plate) the successive scan lines across the imaging plate will tend to be somewhat unevenly spaced apart. Therefore, such multiple scanning head image artifacts can therefore exhibit a repeating pattern in the Y-direction, constituting yet another form of the above discussed "ripple" artifacts. As also noted in the above discussion of ripple artifacts, even very small irregularities in scanning head spacing can give rise to detectable gain artifacts.

Moreover, in addition to the above average or overall differences in detective gain occurring among the various scanning heads (i.e. in which at least one scanning head reads an image to be somewhat lighter or darker than another scanning head, for reasons explained above), a further complication may exist for rotary scanners.

Specifically, for each of the multiple scanning heads in a rotary scanner, the average detective gain will also tend to vary depending upon the radial position of the individual scanning head as the scanning head moves across the imaging plate. This is especially true when the rotary scanner comprises a single stationary photodetector at its center with each scanning head directing phosphorescence emissions back to the centrally located photodetector. In such systems, each of the separate laser beams will rotate on the surface of the photodetector as the scanning head moves across the surface of the imaging plate.

Therefore, when using a multi-head rotary scanner, individual differences in detective gain will exist among the various scanning heads and these differences will also change depending upon the radial position of the scanning head as it moves in a curved path across the imaging plate. Furthermore, such characteristic variations will tend to be unique to each scanning head.

Accordingly, what is desired is a system which both detects, and compensates for, overall variances in detective gain among various different scanning heads, and also compensates for such variances in detective gain among the various scanning heads depending upon the radial position of the scanning head. Such a system would therefore compensate for signal variances in both the X (across the imaging plate) and Y (along the imaging plate) directions.

BRIEF SUMMARY OF THE INVENTION

The present invention provides a variety of methods and systems for detecting and compensating for repeating patterns of variations in scan line distance separation along the length of the imaging plate (i.e.: in the Y-direction), such that "banding" or a "rippled" appearance of the final image can be avoided. In addition, the present invention provides a variety of methods and systems for detecting and compensating for overall variances in detective gain among various different scanning heads, and also compensates for such variances in detective gain among the various scanning heads depending upon the radial position of the scanning head. Thus, the present system advantageously compensates for signal variances in both the X (across the imaging plate) and Y (along the imaging plate) directions.

In a preferred aspect, the present invention provides a method of compensating for differences in detective gain between a plurality of different scanning heads in a multiple scanning head imaging plate scanner, comprising: (a) scanning each of the scanning heads across an imaging plate thereby determining the detected signal at successive locations across the imaging plate for each of the scanning heads; (b) calculating an inverse relationship to the detected signal at successive locations across the imaging plate for each of the scanning heads; (c) scanning each of the scanning heads across an imaging plate containing an image thereon, thereby determining an image value at the successive locations across the imaging plate for each of the scanning heads; and (d) applying the inverse relationship to the determined image values at the successive locations across the imaging plate for each of the scanning heads.

In alternative aspects, the present invention provides a method of compensating for non-uniformity effects in a rotary scanner, comprising: (a) scanning at least one scanning head across an imaging plate thereby determining the detected signal at successive locations across the imaging plate; (b) calculating an inverse relationship to the detected signal at successive locations across the imaging plate; (c) scanning the at least one scanning head across an imaging plate containing an image thereon, thereby determining an image value at the successive locations across the imaging plate; and (d) applying the inverse relationship to the determined image values at the successive locations across the imaging plate.

In alternative aspects, the present invention provides a method of detecting periodic variances in signal values produced by scanning an exposed imaging plate with an imaging plate scanner having at least one scanning head, comprising: (a) moving the exposed imaging plate relative to the imaging plate scanner while repetitively scanning across the imaging plate with the at least one scanning head such that the at least one scanning head scans across the imaging plate in a series of scan lines which are spaced apart along the length of the blank imaging plate; (b) scanning the at least one scanning head across the imaging plate, thereby measuring a detected signal at successive locations along each scan line in the series of spaced apart scan lines; (c) calculating a signal value representative of each of the scan lines in the series of scan lines; and (d) identifying a repeating pattern in the signal values representative of each scan line in the series of spaced apart scan lines.

In alternative aspects, the present invention provides a method of compensating for image artifacts caused by the periodic variances in signal values produced by scanning an exposed imaging plate with an imaging plate scanner having at least one scanning head, comprising: (a) calculating a correction transfer function corresponding to a repeating pattern of the periodic variances in the signal values; (b) scanning the at least one scanning head across an imaging plate containing an image thereon, thereby determining an image value at successive locations across the imaging plate for each scan line in the series of scan lines; and (c) applying the correction transfer function to the determined image values at the successive locations along each of the scan lines passing across the imaging plate.

In alternative aspects, the present invention provides a method of compensating for image artifacts caused by the periodic variances in signal values produced by scanning an exposed imaging plate with an imaging plate scanner having at least one scanning head, comprising: (a) calculating a correction transfer function corresponding to the repeating pattern in the signal values; (b) scanning the at least one scanning head across an imaging plate containing an image thereon, thereby determining an image value at successive locations across the imaging plate for each scan line in the series of scan lines; and (c) varying the speed of relative movement between the imaging plate and the imaging plate scanner in accordance with the correction transfer function.

BRIEF DESCRIPTION OF THE DRAWINGS

FIG. 3 is an illustration of successive scan lines passing across the imaging plate of FIG. 1.

FIG. 4 is a graph of the intensity of the detected signal along a scan line passing across the imaging plate of FIG. 1 in the X-direction.

FIG. 5 is a correction function corresponding to the inverse of the detected signal of FIG. 4.

FIG. 14 is a close up illustration of the repeating pattern of uneven scan lines of FIG. 12.

FIG. 15 is a graph of the average X-directional intensity value of the detected signals across the imaging plate of FIG. 1 plotted along the imaging plate in the Y-direction corresponding to the repeating pattern of FIG. 14. (i.e.: FIG. 15 is a graph of signal values representative of the average intensities of each of the separate scan lines across the imaging plate of FIG. 14).

FIG. 22B is version of the signal of FIG. 21 passed through the modifying transfer function of FIG. 24.

FIG. 23B is a correction transfer function comprising an inverse of the signal of FIG. 22B.

DETAILED DESCRIPTION OF THE DRAWINGS

The present invention provides methods and apparatus which compensate for repeating patterns of "banding" or "rippling" in the appearance of the final image caused by mechanical inaccuracies or vibrations in either an imaging plate scanner or in a transportation system which moves an imaging plate with respect to the imaging plate scanner.

Figure 1:
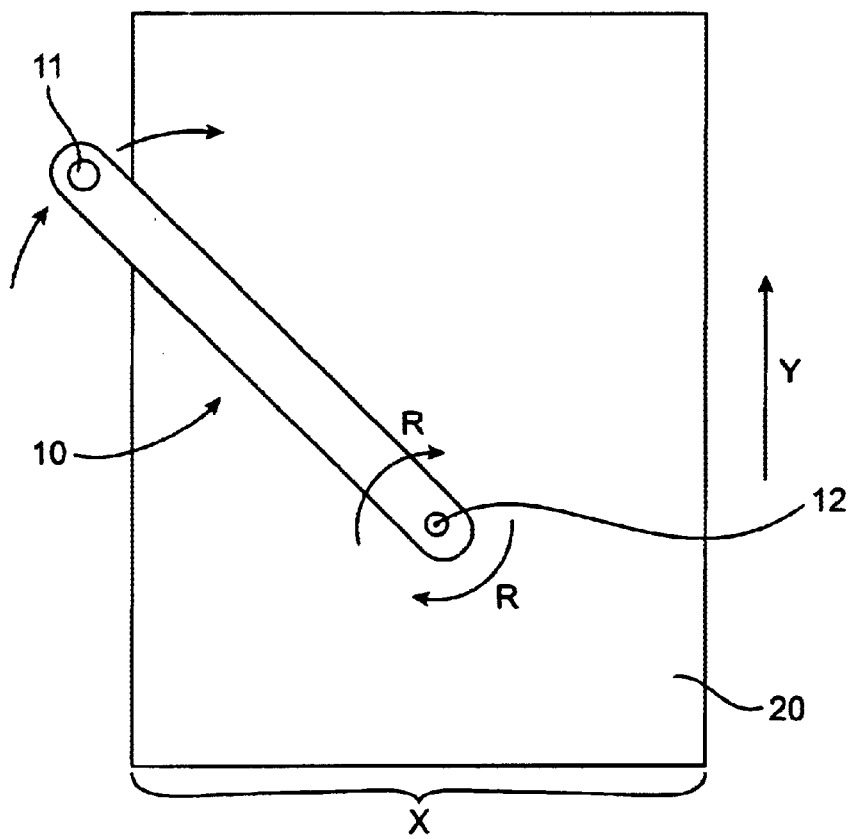
FIG. 1 is a top plan view of an imaging plate passing under a rotating scanner having a single scanning head.
Figure 2:
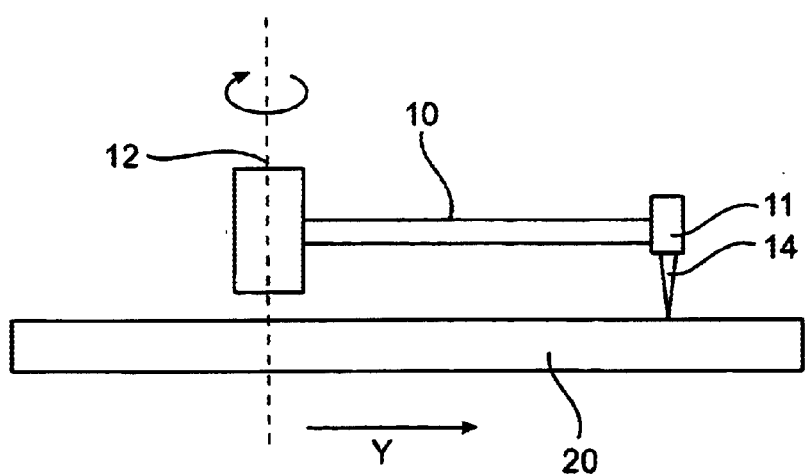
FIG. 2 is a side elevation view of the system of FIG. 1.

(a) Compensation for Image Artifacts Caused By Rotary Scanning Systems:

FIGS. 1 and 2 are schematic illustrations of a rotating one-head scanner 10 having a single scanning head 11. Scanning head 11 focuses a narrow laser beam 14 onto the surface of imaging plate 20. Radiation emitted by imaging plate 20 in response to incident laser beam 14 is then read by scanning head 11 directing such emitted radiation back to a photodetector (which is preferably positioned at or near center 12). As illustrated, scanner 10 rotates in direction R around center 12. Below scanner 10 is positioned an imaging plate 20. Imaging plate 20 has a width X and is moved in direction Y. Accordingly, imaging plate 20 is scanned by scanning head 11 passing quickly across the imaging plate (in the X-direction) while plate 10 is slowly advanced in the Y-direction.

Accordingly, as illustrated in FIG. 3, as scanner 10 is rotated in direction R around a center 12, while imaging plate 20 is advanced in direction Y, scanning head 11 will move across imaging plate 20 in a plurality of spaced apart scan line paths 30.

As can be seen, (due simply to the geometry of the system) scan lines 30 will be spaced apart farther at center 21 of imaging plate 20 and will be spaced closer together at the edges 22 of imaging plate 20. As explained above, the image stored on imaging plate 20 will tend to be darker at those locations where scan lines 30 are spaced farther apart (i.e.: center 21), and will tend to be lighter at those locations where scan lines 30 are spaced closer together (i.e.: edge 22).

Accordingly, when scanning across an imaging plate 20 (for example, an imaging plate 20 which has been exposed to a uniform field of radiation) in direction X along any scan line 30, the detected signal intensity will characteristically vary as signal 40 shown in FIG. 4. Specifically, the signal intensity will be greatest at center 21 (resulting in increased brightness in the center of the image) and will tend to be lowest at the edges 22 (resulting in decreased brightness at the edges of the image).

In accordance with the present invention, methods and systems for compensating for such non-uniformity effects in a rotary scanner are provided, as follows.

Preferably, scanning head 11 is passed across the surface of imaging plate 20 a number of times. An average of the detected signal intensity is then preferably taken at various positions along scan lines 30. Specifically, referring to FIG. 4, a signal intensity (i.e.: an image value) can be measured for each of scan lines 30A, 30B and 30C at each of the column positions X1, X2, etc along scan line 30 in the X direction. Each of these signal intensities can then be averaged to derive a function of the intensity versus column position as shown in FIG. 4. Alternatively, each of these signal intensities can be summed (which would also yield a curve shaped like signal 40). Other mathematical functions can also be used. All that is required within the scope of the present invention is a mathematical function which varies across the width of imaging plate 20 in the X-direction, thus showing the different effects of scanning at the center of the plate (i.e. a darker image) verses scanning at the edges of the plate (i.e. a lighter image).

As shown in FIG. 5, an inverse curve 41 comprising an inverse relationship to signal 40 shown in FIG. 4 can then be calculated such that the product of corresponding points along 40 and 41 will yield a constant function. Inverse curve 41 thus represents a correction factor which can then be multiplied by the individual pixel values of image brightness which are later read (when scanning an imaging plate with an image stored therein) at each of the pixels (at column positions X1, X2, etc.) across the imaging plate.

In one preferred aspect, inverse curve 41 is generated and then stored in computer memory as a lookup table with values corresponding to each of pixels (at column positions X1, X2, etc. across the imaging plate in the X-direction). The values from this lookup table are then multiplied by signal values read by the scanning head when scanning additional imaging plates (ie: when scanning successive imaging plates having images stored therein).

In a preferred aspect, imaging plate 20 has been exposed to a uniform field of irradiation prior to scanning. As such, imaging plate 20 is "blank" (i.e.: it has no image stored thereon). In this case, any variation in signal 40 in the graph of FIG. 4 (from that of a straight line) will be caused by the geometry of the system (specifically, the inherent unevenness in the spacing of successive scan lines passing across the imaging plate with scan lines 30 being farther apart at image plate center 21 and closer together at image plate edges 22).

Thereafter, another image plate 20 having an image stored thereon can be scanned. The resulting image intensity values (i.e. brightness) measured at each of the pixels on the imaging plate can then be multiplied by the values along inverse curve 41. Accordingly, by applying the inverse curve 41 correction factor of FIG. 5 to signal values read by the present rotary scanner, the resulting image will be lightened toward its edges and darkened toward its center, thus minimizing non-uniformity effects (e.g. "edge effects") inherent to the geometry of the rotary scanner.

Signal 40 is thus calculated as a mathematical function of the detected signal measured at various pixel by pixel locations in the X-direction across the imaging plate. In preferred aspects, image values taken along a plurality of scan lines 30 for each column position X1, X2, etc. can be averaged or summed to generate signal 40.

In various preferred aspects, a neighborhood function may also be applied at some or all (or groups of) the various column positions X1, X2, etc. across the imaging plate. Such a neighborhood function operates to remove values which are significantly different from neighboring image values. Such differences can result from dirt specks or scratches on the imaging plate. Since the signal function 40 is expected to be fairly smooth, a median filter can be applied to 40 to remove local spikes which might be caused by dirt, scratches, or other similar noise on the image. For example, a function can be applied to a number of image values taken from a neighborhood about X1 on 40 to derive a replacement for the value at X1 so as to reject outliers which are significantly different from the majority of values in the neighborhood (i.e.: at neighboring column positions X2 and X3). In a preferred aspect, the neighborhood function may comprise a median filter which replaces such outliers with a value equal to the median of nearby "neighboring" values.

In optional aspects of the present invention, a similar neighborhood function may also be applied in the perpendicular (i.e.: Y) direction to the successive scan lines 30 at each column position X1, X2, etc. Specifically, at each column position X1, X2, etc. the values of successive scan lines can be averaged with the neighborhood function rejecting unusually high or low outlier values on scan lines 30.

Figure 6:
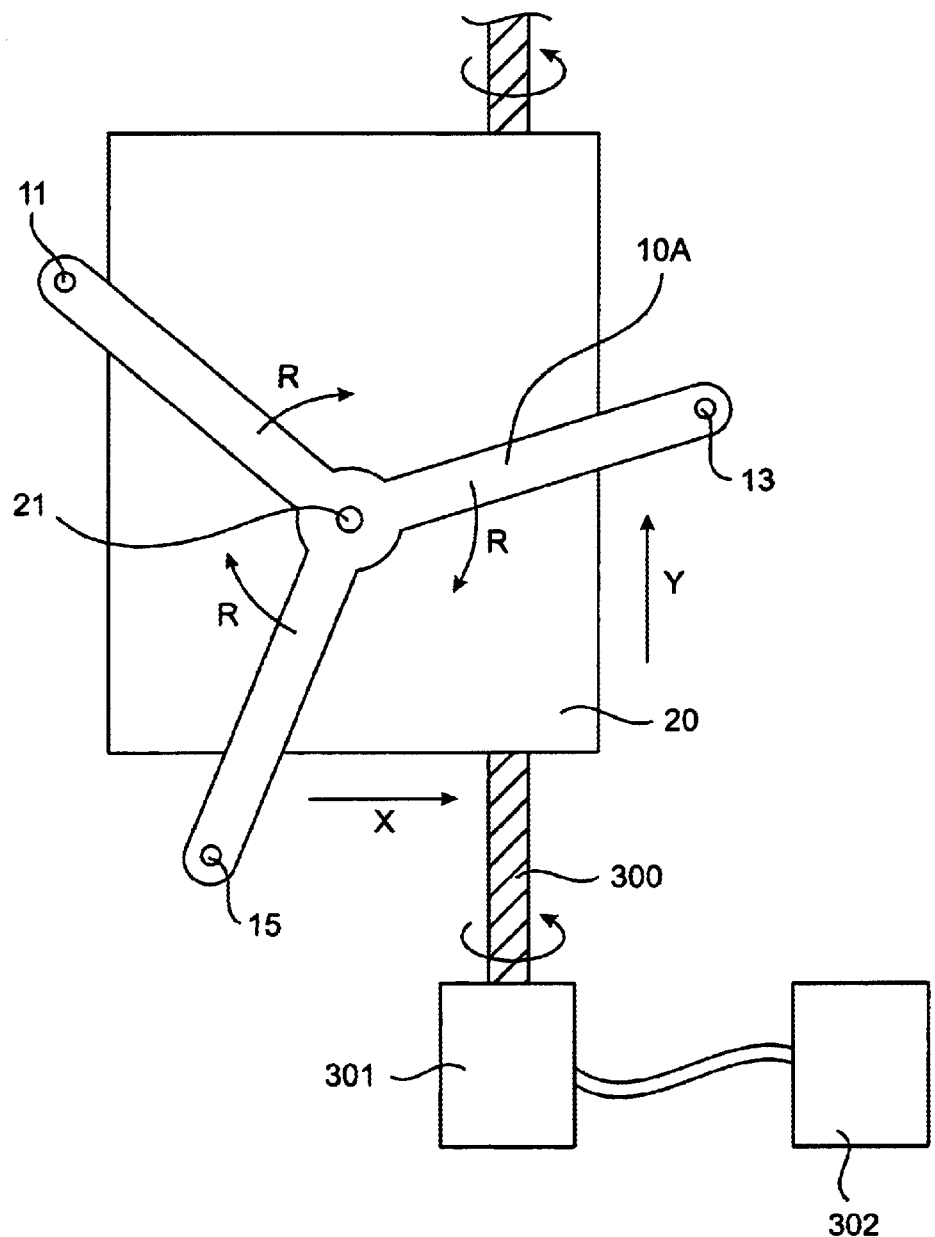
FIG. 6 is an illustration of an imaging plate passing under a rotating three head scanner.

(b) Compensation for Image Artifacts Caused By Differences Among Scanning Heads in Multi-Head Scanning Systems:

The above discussed geometric edge effects (i.e.: progressive darkening of the final image at the edges of the image) are further complicated in the case of a scanner having multiple scanning heads. FIG. 6 illustrates such a multi-head rotary scanner. An example of such a system is found in the Applicants Published PCT Application WO 00/19477.

Specifically, scanner 10A comprises three scanning heads 11, 13 and 15. Scanner 10A is rotated in direction R such that each of scanning heads 11, 13 and 15 pass sequentially over the surface of imaging plate 20.

Preferably, only one of the scanning heads is actively scanning over the surface of imaging plate 20 at a time. This can be accomplished by providing shielding which prevents more than one scanning head from directing an incident laser beam onto imaging plate 20 at a time. Alternatively, each scanning head can have its own dedicated laser with only one laser being turned on at a time. Other approaches are possible. See Applicants Published PCT Application WO 00/19477.

Figure 7:
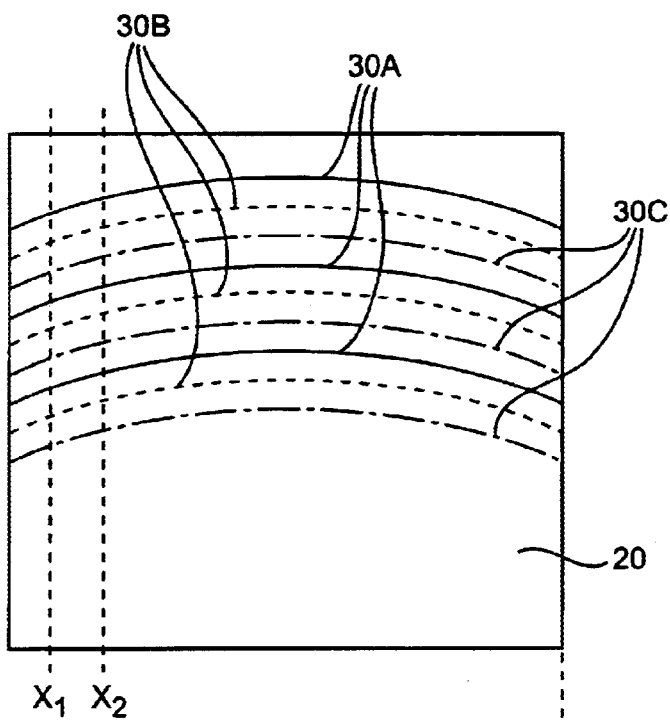
FIG. 7 is a an illustration of successive scan lines taken by each of the three scanning heads passing in the X-direction across the imaging plate of FIG. 6

FIG. 7 illustrates successive scan lines across image plate 20. For example, scanning head 11 first traces a scan line 30A across imaging plate 20. Thereafter, scanning head 13 traces a scan line 30B across imaging plate 20. Thereafter, scanning head 15 traces a scan line 30C across imaging plate 20. Scanner 10A continues to rotate while imaging plate 20 moves in the Y direction. Thus, scanning head 11 again traces a scan line 30A across imaging plate 20, etc. As such, a repeating pattern of successive scan lines (30A, 30B, 30C, 30A, 30B, 30C, etc.) is traced across imaging plate 20.

Figure 8:
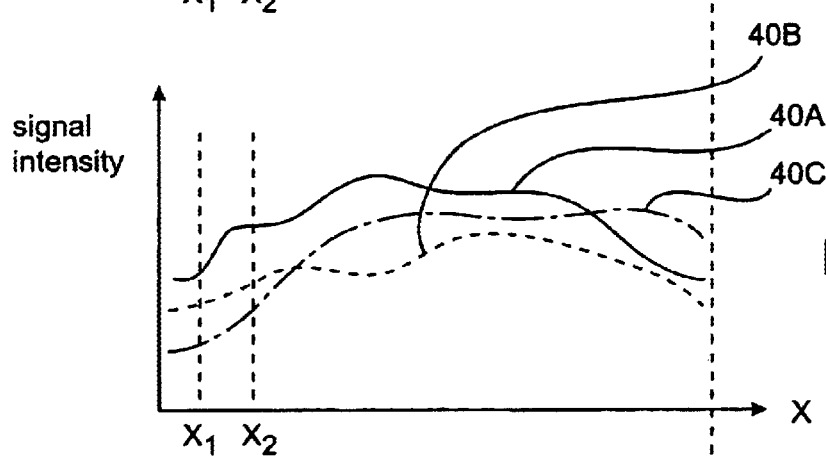
FIG. 8 is a graph of the average detected signal across the imaging plate of FIG. 6 in the X-direction as measured by each of the three separate scanning heads of FIG. 6.

Thereafter, as shown in FIG. 8, each of scan lines 30A can be averaged (or summed, etc.) to generate a signal 40A, each of scan lines 30B are averaged (or summed, etc.) to generate a signal 40B, and each of scan lines 30C are averaged (or summed, etc.) to generate a signal 40C.

Figure 9:
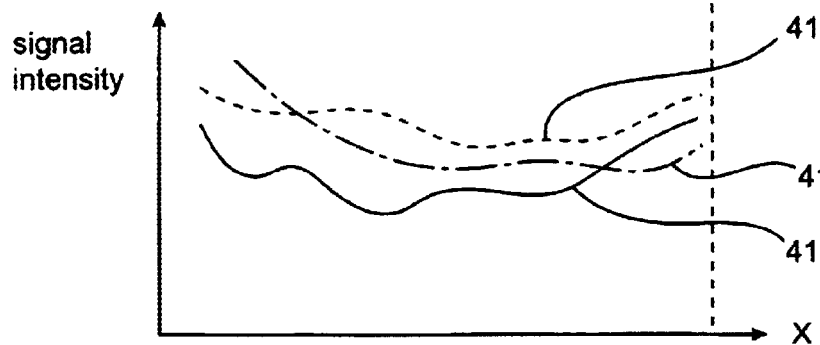
FIG. 9 is a is a correction function corresponding to the inverse of the average detected signal of each of the scanning heads of FIG. 8.

As shown in FIG. 9, the inverse curves of each of signals 40A, 40B and 40C can then be calculated as 41A, 41B and 41C, respectively. These inverse curves 41A, 41B and 41C can then be applied (i.e.: multiplied) as correction factors to signals measured when scanning additional imaging plates by respective scanning heads 11, 13 and 15.

As can also be seen in FIGS. 8 and 9, signals 40A, 40B and 40C need not vary in a uniform manner in the X direction. In other words, although signals 40A, 40B and 40C will tend to be greater toward the center 21 of imaging plate 20 and less towards the edges 22 of imaging plate 20, some variation may well exist to this pattern. Specifically, as can be seen in FIG. 8, variation may exist both among the various scanning heads (ie: signals 40A, 40B and 40C are different from one another), and also for each particular scanning head, variation in signal strength may occur at various column positions X1, X2, etc across the imaging plate. For example, signal 40C may be less than signal 40B at column position X1, but be greater than signal 40B at column position X2.

By calculating inverse curves 41 which vary both for each scanning head (at various pixels corresponding to each of the pixel columns X1, X2, etc. in the X direction) and among the various scanning heads, the present system can be used to generate correction factions which can be applied (i.e.: multiplied to pixel image values) to images extracted by scanning various imaging plates.

(c) Compensation for Ripple (Y-directional) Image Artifacts:

In addition to unwanted image artifacts created by differences in optical paths and scanning head performance when operating a multi-head scanner, unwanted image artifacts may also be created by periodic variance in the speed (in the Y-direction) at which the imaging plate is moved relative to the scanner. Alternatively, such variances may also be caused by vibration normal to the plane of the imaging plate which induce intensity modulation due to the resulting small optical focus changes.

As such, Y-directional ripple image artifacts may occur both in the case of single head scanners which move in a straight path (while advancing an imaging plate thereunder) and in the case of rotary scanners which successively move a number of scanning heads in a curved path over an imaging plate (while advancing an imaging plate thereunder).

Figure 10:
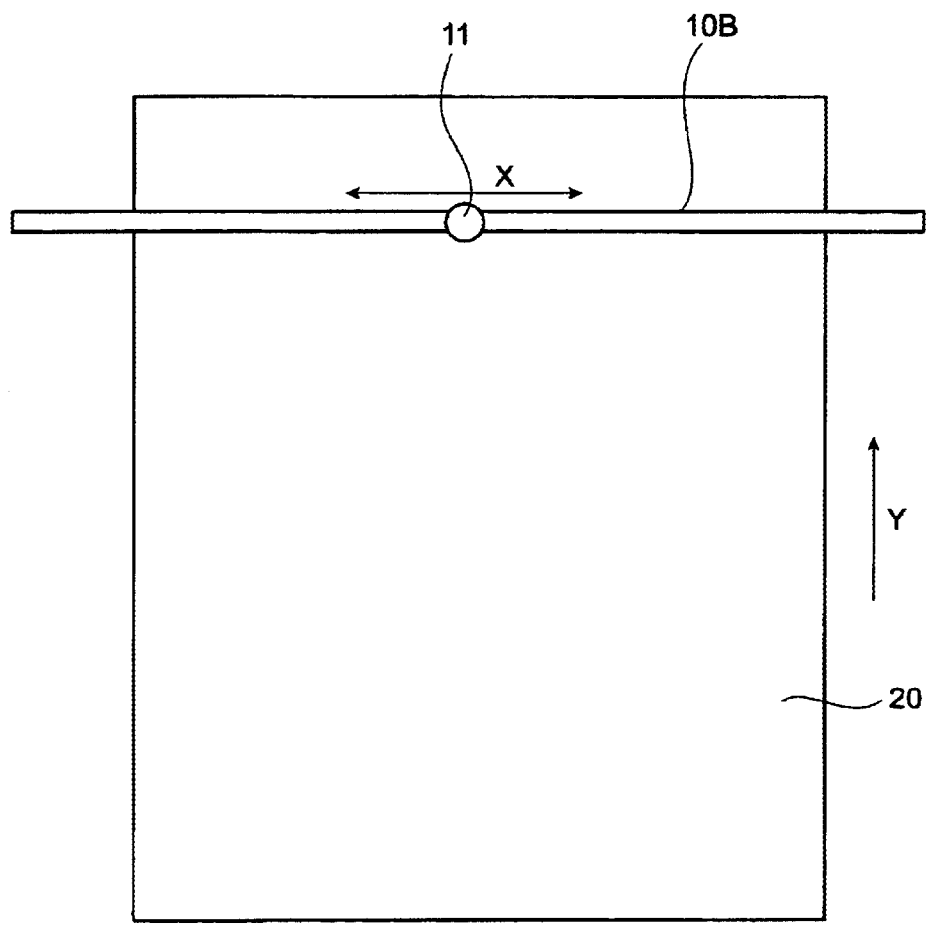
FIG. 10 is an illustration of a reciprocating scanner which moves back and forth as an imaging plate is passed thereunder.
Figure 11A:
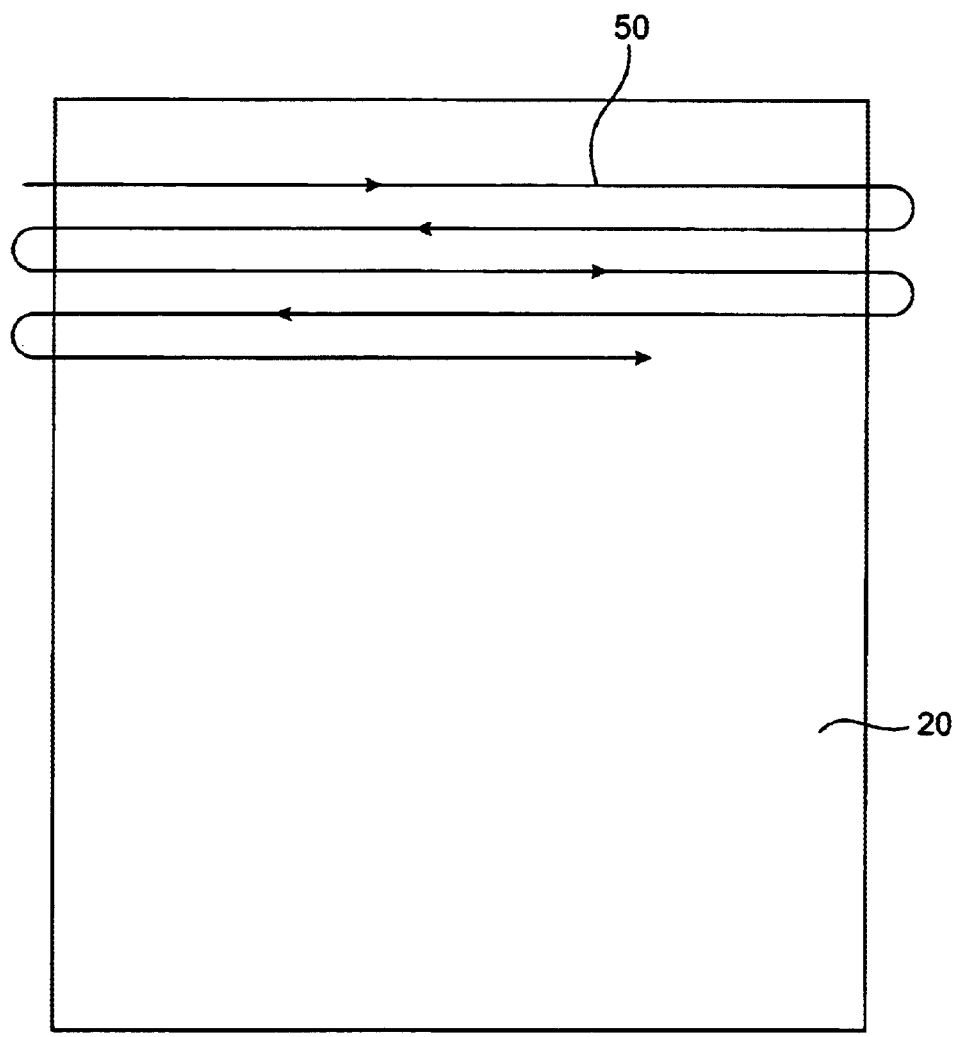
FIG. 11A is an illustration of the raster scan taken by the system of FIG. 10.
Figure 11B:
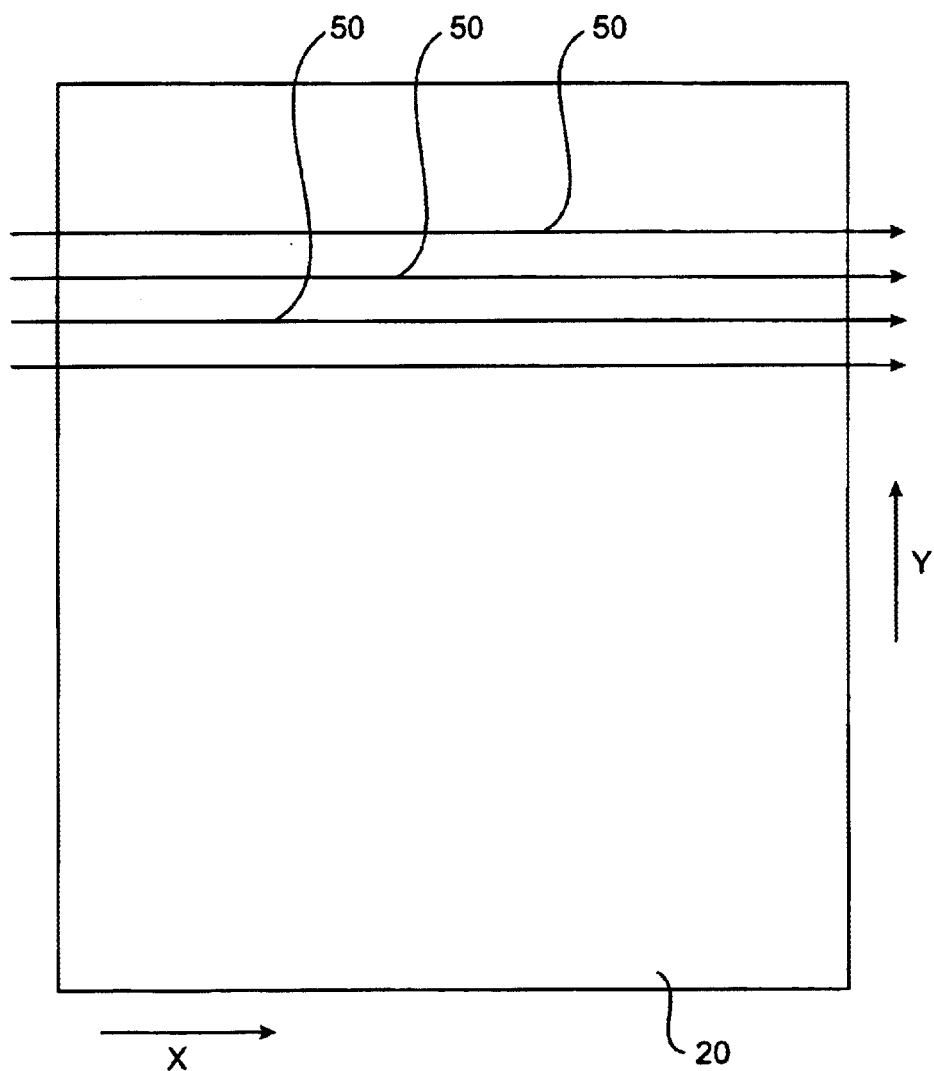
FIG. 11B is an illustration of a scan taken by a typical a linear scanner having a rotating multifaceted mirror which directs a scanning laser beam in a series of straight lines across an imaging plate.
Figure 12:
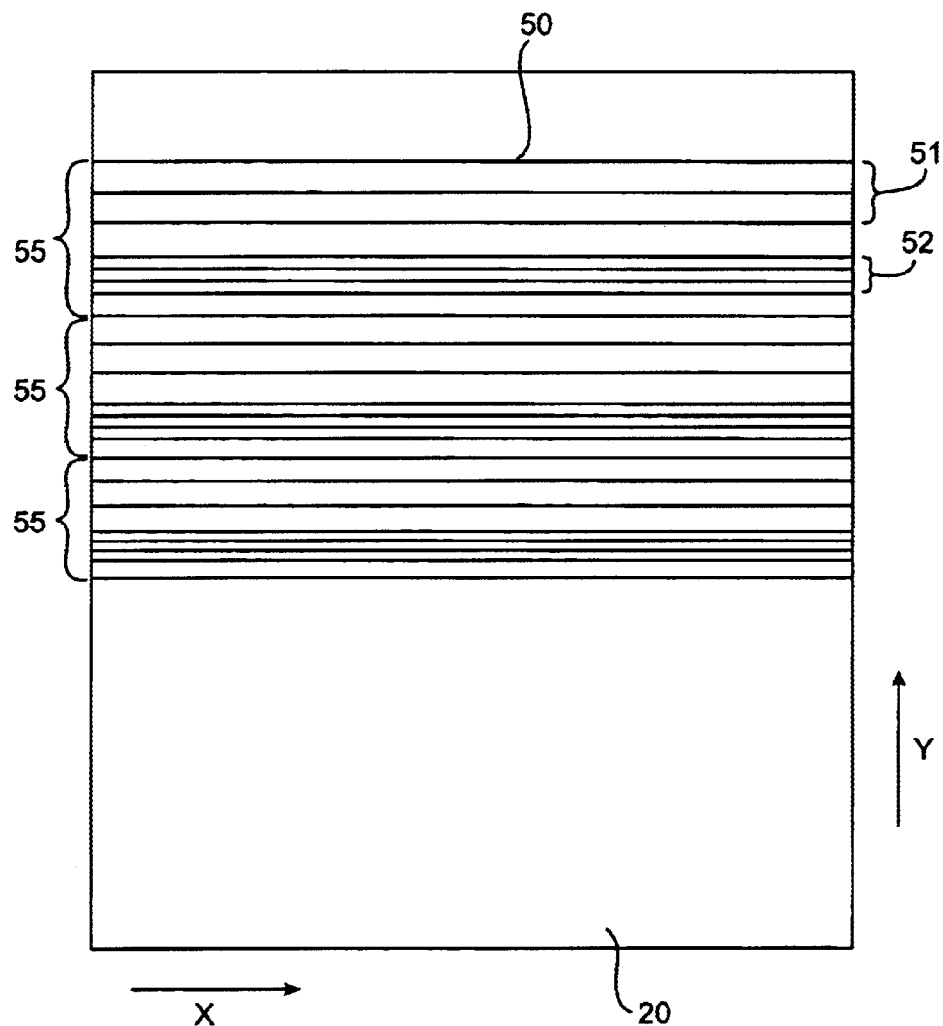
FIG. 12 is an illustration of a repeating pattern of uneven straight scan lines taken across an imaging plate with the system of FIG. 10 or 11B.
Figure 13:
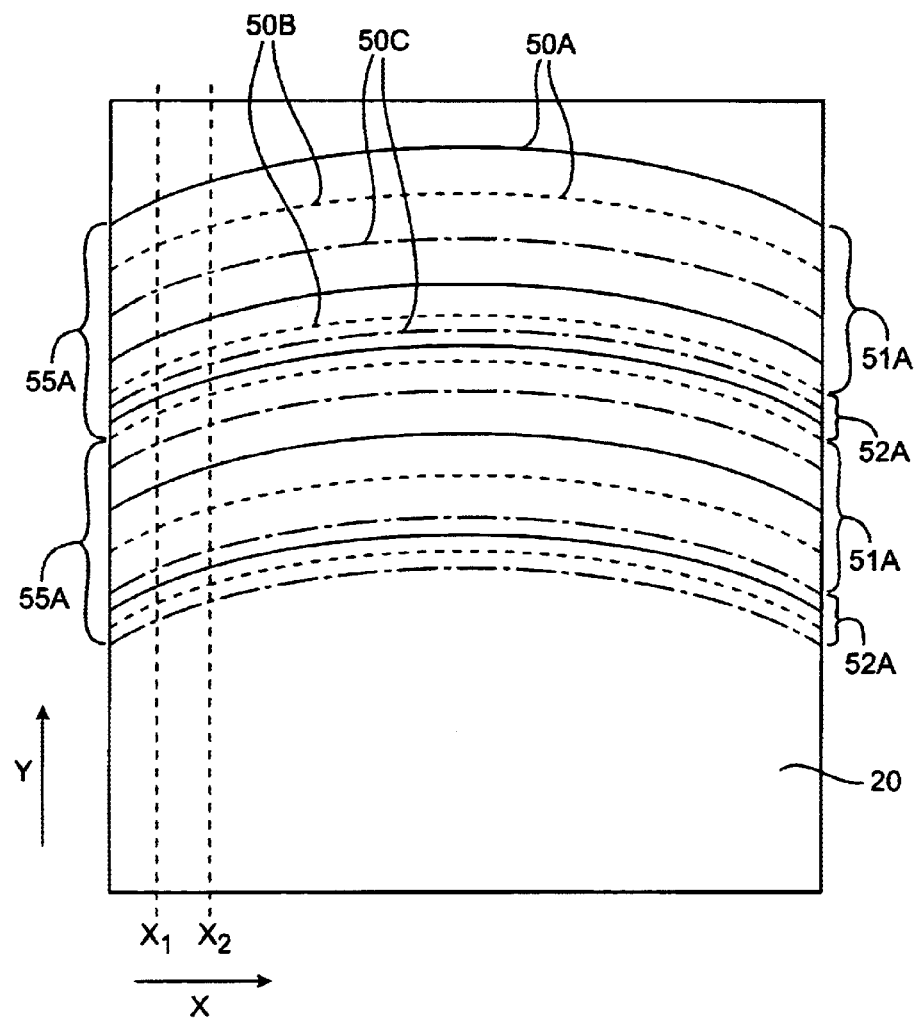
FIG. 13 is an illustration of a repeating pattern of uneven curved scan lines taken across an imaging plate with the rotary scanner of FIG. 6.

FIGS. 10 to 12 illustrate the occurrence of Y-directional ripple image artifacts caused by periodic speed variations in the movement of an imaging plate with respect to a scanner in the case of a single head linear path scanner. A comparable illustration for a multiple head rotary scanner is shown in FIG. 13.

FIG. 10 shows a scanner 10B having a single scanning head 11 which moves back and forth over imaging plate 20 in direction X. Simultaneously with scanning head 11 moving back and forth in direction X (while scanner 10B remains stationary), imaging plate 20 is moved in direction Y. Such movement of imaging plate 20 is preferably periodic such that scanning head first moves fully across imaging plate 20, imaging plate 20 is then advanced an incremental distance and scanning head 11 is then returned (in an opposite direction) across imaging plate 20. Accordingly, a serpentine raster scan line 50 (FIG. 11A) is taken of imaging plate 20.

This same serpentine raster scan line 50 (FIG. 11A) can be generated by a scanner similar to scanner 10B, but instead using a rotating mirror scanning a laser beam back and forth across the surface of the imaging plate (rather than physically moving a scanning head back and forth across the screen) when the imaging plate is advanced in a Y-direction thereunder.

FIG. 11B shows a scan taken by a rotating multifaceted mirror scanner which directs a laser beam in a series of scan lines 50 across imaging plate 20, with each scan line 50 being scanned in the same X direction (rather than back and forth as in FIG. 11A).

As shown in FIG. 12, (which corresponds to either of the scanning systems of FIGS. 10/11A or 11B), differences in the speed at which imaging plate 20 moves in direction Y will result in areas of the imaging plate at which successive scan lines are either spaced farther apart, or closer together. Specifically, successive scan lines 50 may be spaced farther apart in regions 51 and closer together in regions 52. Together, regions 51 and 52 yield a repetitive pattern 55 of varying spacing between scan lines 50.

The illustration of FIG. 12 represents a simplified repeating pattern 55 of repeating ripples having one region where scan lines 50 are close together (region 52) and one region where the scan lines are farther apart (region 51). It is to be understood that typically, repeating pattern 55 may be much more complex, for example, having a different number of spaced apart (51) and bunched together (52) regions and that the scan line spacing may vary in among each of these various regions. For example, some spaced apart regions may be more widely spaced apart than others. This may be due to the fact that repeating pattern 55 may comprise more than one frequency component and that these frequency components may be out of phase with one another. However, in accordance with the present invention, pattern 55 will comprise a regular repeating pattern of scan lines.

FIG. 13 illustrates a similar repeating scan line pattern 55A (having regions 52A in which the scan lines are spaced close together and regions 51A in which the scan lines are spaced far apart). Scan line pattern 55A is an exemplary pattern generated with the rotary three head scanner of FIG. 6. Specifically, scanning head 11 scans lines 50A, scanning head 13 scans lines 50B and scanning head 15 scans lines 50C.

In either the linear scan line pattern 55 taken by a single head scanner moving back and forth (in FIG. 12) or the scan line pattern 55A taken by a rotating three head scanner (in FIG. 13), it can be seen that pattern 55 or 55A is regularly repeating in the Y direction. Moreover, in the case of a rotating three head scanner, it can be seen that the repeating pattern is independent of which particular scanning head which is passing across the imaging plate. For example, pattern 55A may repeat over a number of scan lines wherein this number is not a multiple of three (in the case of a three head scanner).

In accordance with the present invention, a system for detecting periodic variations in signal values produced by scanning an exposed imaging plate with an imaging plate scanner having at least one scanning head is provided, as follows.

In accordance with the present invention, repeating pattern 55 (or 55A) is identified. After identifying the repeating pattern 55 (or 55A) a correction transfer function can be calculated corresponding to this repeating pattern. This correction transfer function can then be applied to image values read at each of the pixels in a scanned imaging plate, thereby appropriately adjusting the brightness of the image at each of the pixels (across the imaging plate in the X direction) to compensate for image artifacts caused by periodic variances in signal values.

In accordance with preferred aspects, the present system may identify repeating pattern 55 or 55A as follows.

FIG. 14 shows a close up illustration of a repeating pattern 55 of uneven scan lines 50 having a number of different regions where the scan lines are spaced apart (regions 51) and close together (regions 52). FIG. 15 is a graph of signal 60, representing the intensity of the detected signals taken in the X-direction along scan lines 50 of the imaging plate of FIG. 14, as plotted in the Y-direction corresponding to the repeating pattern of FIG. 14. (i.e.: FIG. 15 is a graph of signal values representative of each of the separate scan lines of FIG. 14).

In preferred aspects, signal 60 is calculated such that each point therealong is representative of a signal value corresponding to a scan line 50. For example, point 60A corresponds to a value which is representative of scan line 50A and point 60B corresponds to a value which is representative of scan line 50B, etc. In preferred aspects, point 60A is simply an average of each of the pixel by pixel values along line 50A (i.e.: an average of the values at pixels X1, X2, etc. along line 50A). Alternatively, point 60A can be a summation of each of the pixel by pixel values along line 50A (i.e.: an average of the values at pixels X1, X2, etc. along line 50A). Other mathematical functions are also considered.

As can be seen, signal 60 will tend to be highest at those locations where the successive scan lines 50 are farthest apart, and signal 60 will tend to be lowest at those locations where the successive scan lines 50 are closest together. Stated another way, bright bands extending across the final image will tend to occur in regions 51, whereas darker bands extending across the final image will tend to occur in regions 52.

In accordance with the present invention, the repeating pattern 55 (or 55A) of signal 60 is then identified. This may be accomplished in a number of ways.

Figure 16:
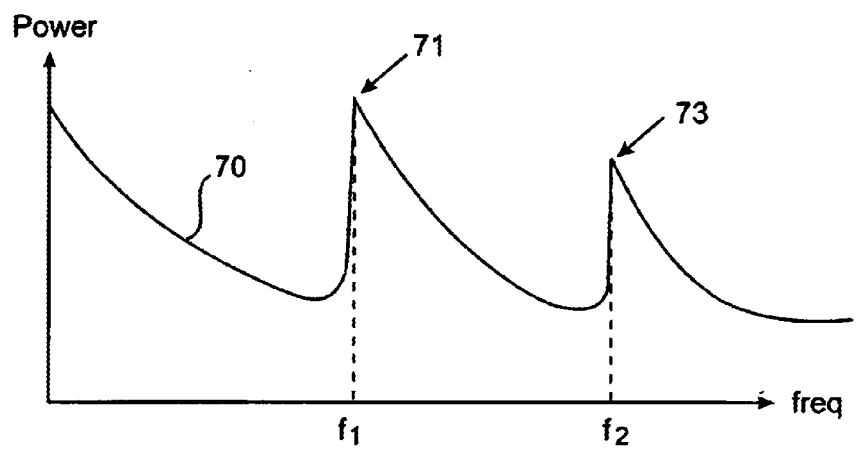
FIG. 16 is a power spectrum analysis of the signals representative of each of the scan lines in FIG. 15, showing frequency components of the repeating pattern of FIG. 14.

For example, after signal 60 has been computed, the present invention may then calculate the frequency components of the repeating pattern. This may be done in a variety of ways. Most preferably, a spectrum estimation of signal 60 can be performed, thereby generating a power spectrum of signal 60. In one preferred aspect, a Fourier transform is applied to signal 60 to determine at which frequency or frequencies signal 60 repeats itself. FIG. 16 illustrates a signal 70 which is a Fourier transform of signal 60. Signal 70 has peaks 71 and 73. Peaks 71 and 73 correspond to frequencies f1 and f2. Similarly, other techniques for identifying repeating patterns in a signal like 60 can be applied, for example, a Maximum-Entropy spectrum estimation could be performed instead of a Fourier transform.

Figure 17:
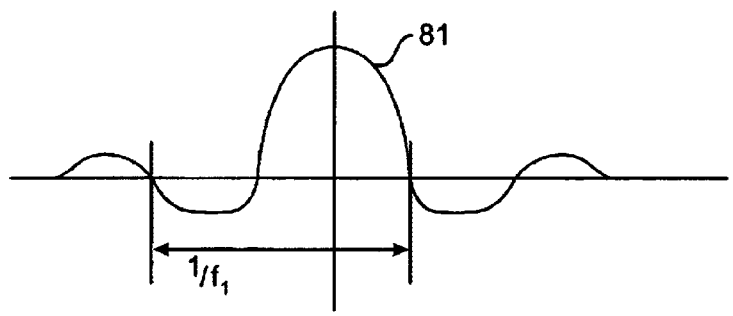
FIG. 17 is a spatial filter tuned to a first frequency of the power spectrum of FIG. 16.
Figure 18:
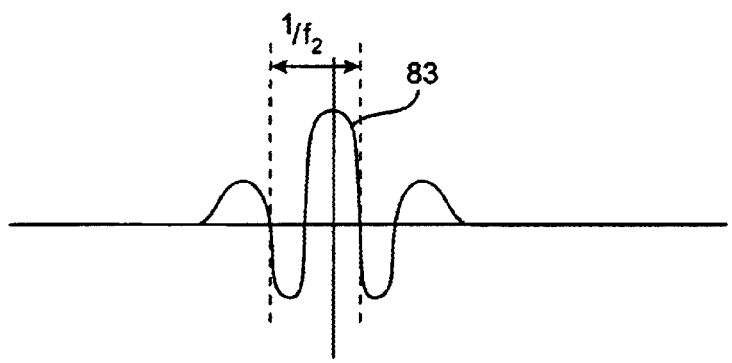
FIG. 18 is a spatial filter tuned to a second frequency of the power spectrum of FIG. 16.
Figures 19, 20, 21:
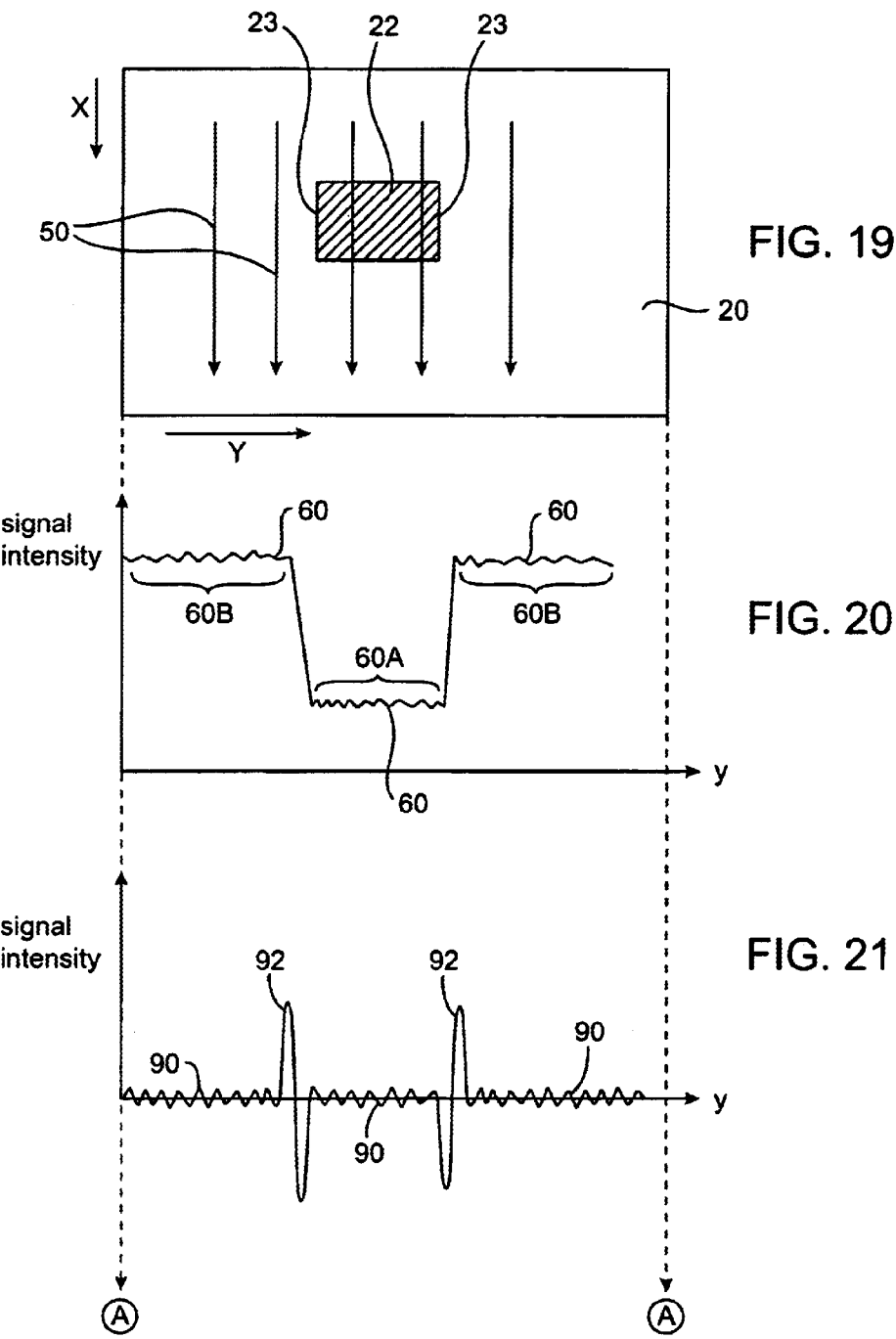
FIG. 19 is an illustration of scan taken across an image plate having a rectangular image thereon.
FIG. 20 is a graph similar to FIG. 15, showing the average X-directional intensity value of the detected signal taken along a scan lines passing across the imaging plate of FIG. 19 plotted along the imaging plate in the Y-direction.
FIG. 21 is a signal resulting from a spatial filter convolved to the detected signal of FIG. 20.

FIG. 17 illustrates a spatial filter 81 tuned to frequency f1 and FIG. 18 illustrates a spatial filter 83 tuned to frequency f2. These spatial filters 81 and 83 may then be applied to signals representing images read from (additional) imaging plates to yield preferred correction transfer functions. Specifically, spatial filters 81 and 83 are convolved with the signal 60 which has been derived from a subsequent scanned plate (i.e.: the plate of FIG. 19) to yield a filtered signal 90 as shown in FIG. 21. This filtered signal 90 is then manipulated to derive a multiplicative correction function 100 as shown in either of FIG. 23A or 23B. Values in this correction function 100 are then used as multiplicative scale factors to adjust the brightness of pixel values on corresponding lines of the original scanned image thereby reducing the amplitude of the ripple artifacts.

Alternatively, the present correction transfer function may comprise a subtractive correction in which a correction function derived from the filtered signal 90 is added to, pixels on corresponding lines of the image. In this case, the correction transfer function will preferably be centered around zero. (In contrast, a multiplicative correction transfer function will preferably be centered around 1.0).

In further optional aspects of the present invention, the introduction into the image of undesired artifacts by the above ripple correction process is accomplished by clipping excessively large amplitude corrections in the resultant image signal generated by applying the correction transfer function to the measured image values at successive locations along each of the scan lines. Large amplitude swings 92 in the filtered signal 90 can result from occurrences such as step edges in the image (FIG. 21). If uncorrected, such large amplitude swings 92 will result in an incorrect correction of the image which can result in the introduction of spurious ripples surrounding sharp horizontal edges in the image. Such "clipping" of the signal is desirable as a system to prevent such large amplitude variations in the correction transfer function, as follows.

FIG. 19 illustrates an imaging plate 20 having a darkened rectangular image 25 thereon which exhibits sharp edges aligned with the X axis (which is displayed vertically in the figure). Imaging plate 20 is scanned with successive scan lines 50 passing thereover, as shown. FIG. 20 illustrates a signal 60 similar to that of FIG. 15. As can be seen, those scan lines 50 which pass over darkened image 22 will show up as a darkened region 60A, whereas those regions in which scan lines 50 do not pass over darkened image 22 will show up as lightened regions 60B. Accordingly, ripple pattern 55 can exist in both regions 60A and 60B but at different brightness levels.

In accordance with a preferred aspect of the present invention, convolving signal 60 with a filter tuned to an aspect of the ripple (for example, filter 81 or 83) results in a zero centered signal 90 (FIG. 21).

Due to the sharp edges 23 on darkened image 22 running parallel to scan lines 50, a large amplitude jump will be seen between signals 60A and 60B. When spatial filters are applied to signal 60, a convolution signal 90 having large amplitude peaks 92 (FIG. 21) will be generated. In accordance with a preferred aspect, peaks 92 will then be clipped (i.e.: their maximum amplitude will be limited to 92A) above a predetermined maximum amplitude as shown in clipped signal 90A in FIG. 22A.

Figure 22A:
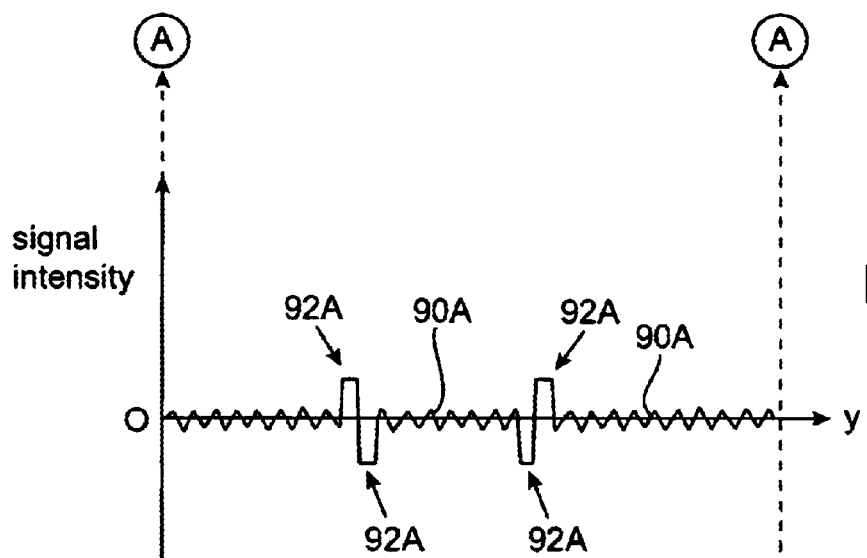
FIG. 22A is a "clipped" version of the signal of FIG. 21.
Figure 23A:
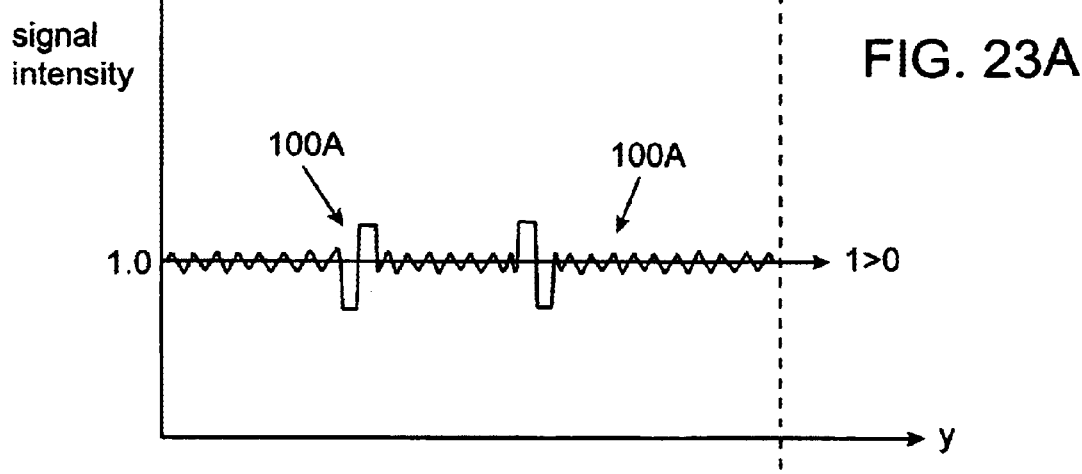
FIG. 23A is a correction transfer function comprising an inverse of the signal of FIG. 22A.

In accordance with the a preferred aspect of the present invention, a correction transfer function can then be generated from clipped signal 90A in FIG. 22A. In the case of multiplicative correction (which is a preferred aspect of the present system), the clipped signal 90A of FIG. 22A is scaled by a negative factor that adjusts the degree of correction to be applied and a value of 1.0 is then added to this result. FIG. 23A shows the result of applying this derivation to clipped signal 90A of FIG. 22A, resulting in correction transfer function 100A.

Figure 24:
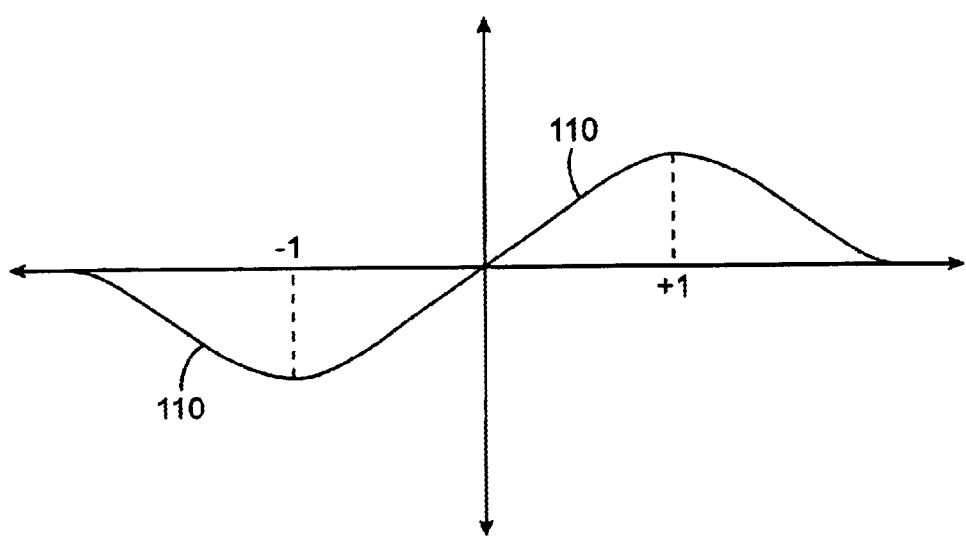
FIG. 24 is an illustration of a modifying transfer function which progressively suppresses larger amplitude inputs to zero, while leaving smaller amplitude inputs unchanged.

FIG. 24 illustrates a modifying transfer function 110 which can be applied to signal 90 of FIG. 21 (as an alternative to clipping high amplitudes as shown in FIG. 22A). FIG. 22B shows the application this modifying transfer function 110 (FIG. 24) applied to signal 90 of FIG. 21 resulting in modified signal 90B. As can be seen, modifying transfer function 110 progressively suppresses larger amplitude inputs to zero (flattened regions 93), while leaving smaller amplitude inputs unchanged. Thus peaks 92 (in FIG. 21) are instead substantially flattened (and appear as flattened regions 93) after the application of modifying transfer function 110 to signal 90 (with minimal or no change being made to the lower amplitude values of signal 90.

In the case of multiplicative correction (which is a preferred aspect of the present system), the modified signal 90B of FIG. 22B is scaled by a negative factor that adjusts the degree of correction to be applied and a value of 1.0 is then added to this result. FIG. 23B shows the result of applying this derivation to modified signal 90B of FIG. 22B, resulting in correction transfer function 100B.

In accordance with another preferred aspect of the present invention, the ripple suppression technique (i.e.: Compensation for Ripple (Y-directional) Image Artifacts) described above can also be adapted to suppress residual artifacts arising from non-uniformities inherent in a multi-headed scanner. Although the above technique substantially reduces such artifacts, some residual artifacts can still remain. For example, in the case of a three head scanner (FIG. 6), there a small ripple artifact having a three line period may still remain in the image even after compensating for Y-directional ripple artifacts using the above technique.

Therefore, in accordance with an optional preferred aspect of the present invention, a tuned filter can be designed to detect the ratio of average amplitudes between image lines arising from a single scanner head versus the average amplitudes from all of the scan heads in an area of the scanned image. This ratio can be used to scale the amplitude of the selected scan head's pixel by pixel detected image values in that area to more closely match the average value in that area. Preferably, this process may be repeated for each of the scan heads thereby causing the average signal amplitude in the area to be more closely matched for each of the individual scan heads.

In optional preferred aspects of the present invention, a system is provided for compensating for image artifacts produced by variations in the Y-directional speed of the imaging plate with respect to the scanner, as follows.

Referring back to FIG. 6, a worm gear 300 is used to move imaging plate 20 in the Y-direction. It is to be understood that imaging plate 20 is preferably mounted on top of a shuttle (not shown) which is actually moved by worm gear 300. A rotary drive mechanism 310 turns worm gear 300. Rotary drive mechanism 310 preferably comprises a reference system for determining the rotation angle of worm gear 300. A computer control system 302 controls the speed of rotation of rotary drive mechanism 310 which in turn controls the speed of rotation of worm gear 300. Computer system 310 may comprise a table of delay times or a timer which determines the timing between successive steps of rotary drive mechanism 310.

In accordance with a preferred aspect of the present invention, computer control system 302 varies the speed of rotation of rotary drive mechanism 310 in accordance with the above calculated correction transfer function. As such, rotary drive mechanism 310 speeds up the Y-directional motion of imaging plate 20 at those times that the corrective transfer function indicates that the scan lines would otherwise be too close together. Conversely, rotary drive mechanism 310 slows down the Y-directional motion of imaging plate 20 at those times that the corrective transfer function indicates that the scan lines would otherwise be too far apart.

In optional preferred aspects, rotary drive mechanism 310 may comprise a stepper motor. In optional preferred aspects, the reference system for determining the rotation angle of worm gear 300 may comprise an encoder wheel, or a once around index pulse, thereby allowing the counting of steps of the stepper motor 310 with respect to the once around index pulse, to determine the rotation angle of rotary drive 310 relative to a particular rotary position.

In addition, (including instances where different forms of imaging plate transport are used), periodic speed variations in the imaging plate transport (i.e.: in the Y-direction) can result from mechanical asymmetries such as a slightly off center bore on a screw drive or the non-uniform engagement of gear teeth. Since the phasing of such speed variations is often consistently tied to the orientation of a drive shaft at an appropriate point in the drive chain, it is possible to suppress the speed variations by driving that shaft at slightly faster or slower speeds in opposition to the known speed error at the imaging plate. In preferred aspects, an encoder is attached to the shaft to determine its orientation and that value is used to access a table of stored speed adjustments which are then employed to speed up or slow down the drive motor. In an alternate preferred aspect, where a stepper motor is employed for driving the shaft, it is sufficient to use a once-around sensor to determine when the shaft returns to an original position. The orientation of the shaft can then be estimated by the number of motor steps taken relative to the last once-around trigger.

Accordingly, the present invention provides a method of compensating for image artifacts caused by the periodic variances in signal values produced by scanning an exposed imaging plate with an imaging plate scanner having at least one scanning head, comprising: (a) calculating a correction transfer function corresponding to the repeating pattern in the signal values; (b) scanning the at least one scanning head across an imaging plate containing an image thereon, thereby determining an image value at successive locations across the imaging plate for each scan line in the series of scan lines; and (c) varying the speed of relative movement between the imaging plate and the imaging plate scanner in accordance with the correction transfer function.

In preferred aspects, this method comprises varying the speed of relative movement between the imaging plate and the imaging plate scanner in accordance with the correction transfer function, specifically, (i) speeding up the relative motion at those times that the corrective transfer function indicates that the scan lines would otherwise be too close together, and (ii) slowing down the relative motion at those times that the corrective transfer function indicates that the scan lines would otherwise be too far apart.

Throughout the present application, reference is made to the scanner being kept at a fixed location with the imaging plate moved thereunder. It is to be understood that, in accordance with the present invention, the imaging plate may instead be kept at a fixed location with the scanner moved thereover. Also, both the scanner and the imaging plate case be moved to produce the relative motion between the scanner and the imaging plate (which moves successive scan lines down the length of the imaging plate).

What is claimed is:

1. A method of compensating for differences in detective gain between a plurality of different scanning heads in a multiple scanning head imaging plate scanner, comprising:
   (a) scanning each of the scanning heads across an imaging plate thereby determining the detected signal at successive locations across the imaging plate for each of the scanning heads;
   (b) calculating an inverse relationship to the detected signal at successive locations across the imaging plate for each of the scanning heads;
   (c) scanning each of the scanning heads across an imaging plate containing an image thereon, thereby determining an image value at the successive locations across the imaging plate for each of the scanning heads; and
   (d) applying the inverse relationship to the determined image values at the successive locations across the imaging plate for each of the scanning heads.

2. The method of claim 1, wherein the imaging plate in (a) has been exposed to a uniform field of irradiation.

3. The method of claim 1, wherein determining the detected signal at successive locations across the imaging plate for each of the scanning heads comprises:
   scanning each of the scanning heads across the blank imaging plate a number of times; and
   calculating an average of the detected signal at each of the successive locations across the imaging plate for each of the scanning heads.

4. The method of claim 3, wherein the imaging plate is moved with respect to the scanner such that each of the scanning heads move across the imaging plate a number of times, passing over the imaging plate in a series of scan lines which are spaced apart along the length of the imaging plate.

5. The method of claim 1, wherein determining the detected signal at successive locations across the imaging plate for each of the scanning heads comprises:
   calculating a mathematical function of the detected signal across the imaging plate for each of the scanning heads.

6. The method of claim 5, wherein calculating a mathematical function of the detected signal across the imaging plate comprises:
   averaging the detected signal across the imaging plate for each of the scanning heads.

7. The method of claim 5, wherein calculating a mathematical function of the detected signal across the imaging plate comprises:
   summing the detected signal across the imaging plate for each of the scanning heads.

8. The method of claim 5, wherein calculating an inverse relationship comprises:
   calculating an inverse to the mathematical function of the detected signal at successive locations across the imaging plate for each of the scanning heads.

9. The method of claim 1, wherein determining the detected signal at successive locations across the imaging plate for each of the scanning heads comprises:
   tabulating detected signal values at successive locations across the imaging plate for each of the scanning heads.

10. The method of claim 9, wherein a detected signal value is tabulated for each successive pixel across the imaging plate.

11. The method of claim 9, wherein calculating an inverse relationship comprises:
    generating a lookup table comprising inverse values to the tabulated detected signal values at successive locations across the imaging plate for each of the scanning heads.

12. The method of claim 1, wherein (c) and (d) are repeated using additional imaging plates having images stored thereon.

13. The method of claim 1, wherein the multiple scanning head imaging plate scanner has three scanning heads which pass in sequence over the imaging plate.

14. The method of claim 1, wherein determining the detected signal at successive locations across the imaging plate for each of the scanning heads further comprises:
    applying a neighborhood function to the detected signal.

15. The method of claim 14, wherein the neighborhood function comprises a median filter.

16. A method of compensating for non-uniformity effects in a rotary scanner, comprising:
    (a) scanning at least one scanning head across an imaging plate thereby determining the detected signal at successive locations across the imaging plate;

(b) calculating an inverse relationship to the detected signal at successive locations across the imaging plate;

(c) scanning the at least one scanning head across an imaging plate containing an image thereon, thereby determining an image value at the successive locations across the imaging plate; and (d) applying the inverse relationship to the determined image values at the successive locations across the imaging plate.

17. The method of claim 16, wherein the imaging plate in (a) has been exposed to a uniform field of irradiation.

18. The method of claim 16, wherein determining the detected signal at successive locations across the imaging plate for each of the scanning heads comprises:

scanning the at least one scanning head across the blank imaging plate a number of times; and calculating an average of the detected signal at each of the successive locations across the imaging plate.

19. The method of claim 18, wherein the at least one scanning head comprises a single scanning head.

20. The method of claim 18, wherein the at least one scanning head comprises a plurality of scanning heads and wherein the detected signal at successive locations across the imaging plate is separately determined for each of the plurality of scanning heads.

21. The method of claim 20, wherein the plurality of scanning heads comprise three scanning heads.

22. The method of claim 16, wherein determining the detected signal at successive locations across the imaging plate for each of the scanning heads comprises:

calculating a mathematical function of the detected signal across the imaging plate.

23. The method of claim 22, wherein calculating a mathematical function of the detected signal across the imaging plate comprises:

averaging the detected signal across the imaging plate.

24. The method of claim 22, wherein calculating a mathematical function of the detected signal across the imaging plate comprises:

summing the detected signal across the imaging plate.

25. The method of claim 22, wherein calculating an inverse relationship comprises:

calculating an inverse to the mathematical function of the detected signal at successive locations across the imaging plate.

26. The method of claim 16, wherein determining the detected signal at successive locations across the imaging plate comprises:

tabulating detected signal values at successive locations across the imaging plate for each of the scanning heads.

27. The method of claim 26, wherein a detected signal value is tabulated for each successive pixel across the imaging plate.

28. The method of claim 26, wherein calculating an inverse relationship comprises:

generating a lookup table comprising inverse values to the tabulated detected signal values at successive locations across the imaging plate for each of the scanning heads.

29. The method of claim 26, wherein (c) and (d) are repeated using additional imaging plates having images stored thereon.

30. The method of claim 16, wherein determining the detected signal at successive locations across the imaging plate for each of the scanning heads further comprises:

applying a neighborhood function to the detected signal.

31. The method of claim 30, wherein the neighborhood function comprises a median filter.

32. A method of detecting periodic variances in signal values produced by scanning an exposed imaging plate with an imaging plate scanner having at least one scanning head, comprising:

(a) moving the exposed imaging plate relative to the imaging plate scanner while repetitively scanning across the imaging plate with the at least one scanning head such that the at least one scanning head scans across the imaging plate in a series of scan lines which are spaced apart along the length of the blank imaging plate;

(b) scanning the at least one scanning head across the imaging plate, thereby measuring a detected signal at successive locations along each scan line in the series of spaced apart scan lines;

(c) calculating a signal value representative of each of the scan lines in the series of scan lines; and (d) identifying a repeating pattern in the signal values representative of each scan line in the series of spaced apart scan lines.

33. The method of claim 32, wherein at least a portion of the periodic variances in signal values produced by an imaging plate scanner comprise periodic speed variances in relative movement between the imaging plate and the imaging plate scanner.

34. The method of claim 32, wherein calculating a signal value representative of each of the scan lines in the series of scan lines comprises:

calculating an average signal value along the scan line.

35. The method of claim 32, wherein calculating a signal value representative of each of the scan lines in the series of scan lines comprises:

summing the signal values of each of the various pixels disposed along the scan line.

36. The method of claim 32, wherein identifying a repeating pattern in the signal values comprises:

calculating one or more frequency components of the repeating pattern.

37. The method of claim 36, wherein calculating one or more frequencies components of the repeating pattern comprises:

performing a spectrum estimation on the signal values representative of each of the scan lines in the series of scan lines, thereby generating a power spectrum of the signal values.

38. The method of claim 37, wherein performing a spectrum estimation comprises:

applying a Fourier transform to the signal values representative of each of the scan lines in the series of scan lines.

39. The method of claim 37, wherein performing a spectrum estimation comprises:

applying a Maximum-Entropy spectrum estimation to the signal values representative of each of the scan lines in the series of scan lines.

40. The method of claim 32, further comprising compensating for image artifacts caused by the periodic variances in signal values, by:

(e) calculating a correction transfer function corresponding to the repeating pattern in the signal values;

(f) scanning the at least one scanning head across an imaging plate containing an image thereon, thereby determining an image value at successive locations across the imaging plate for each scan line in the series of scan lines; and (g) applying the correction transfer function to the determined image values at the successive locations along each of the scan lines passing across the imaging plate.

41. The method of claim 40, wherein at least a portion of the periodic variances in signal values produced by an imaging plate scanner comprise periodic speed variances in relative movement between the imaging plate and the imaging plate scanner.

42. The method of claim 40, wherein moving the imaging plate relative to the imaging plate scanner comprises:

moving the imaging plate while the scanner remains positioned at a constant location.

43. The method of claim 40, wherein moving the imaging plate relative to the imaging plate scanner comprises:

moving the scanner while the imaging plate remains positioned at a constant location.

44. The method of claim 40, wherein (f) and (g) are repeated using additional imaging plates having images stored thereon.

45. The method of claim 40, wherein calculating a correction transfer function comprises:

calculating at least one spatial detection filter corresponding to the repeating pattern.

46. The method of claim 45, wherein the at least one spatial detection filter is tuned to a frequency component of the repeating pattern.

47. The method of claim 45, wherein the at least one spatial detection filter is tuned to a summation of a plurality of frequency components of the repeating pattern.

48. The method of claim 40, wherein calculating a correction transfer function comprises:

calculating a subtractive function.

49. The method of claim 48, wherein applying the correction transfer function to the determined image values comprises:

adding correction values to the detected signal measured at successive locations along each scan line, thereby uniformly adjusting image brightness along the scan line.

50. The method of claim 40, wherein calculating a correction transfer function comprises:

calculating a multiplicative function.

51. The method of claim 50, wherein applying the correction transfer function to the determined image values comprises:

multiplying the detected signal measured at successive locations along each scan line by a scale factor derived from the multiplicative function.

52. The method of claim 50, wherein the multiplicative function comprises an inverse of detected signal values representative of each of the scan lines in the series of scan lines.

53. The method of claim 40, further comprising:

(h) clipping large amplitude corrections in a resultant image signal generated by applying the correction transfer function to the determined image values at the successive locations along each of the scan lines passing across the imaging plate in (g).

54. The method of claim 40, further comprising:

(h) applying a modifying transfer function to a resultant image signal generated by applying the correction transfer function to the determined image values at the successive locations along each of the scan lines passing across the imaging plate in (g), wherein the modifying transfer function progressively suppresses larger amplitudes in the resultant image signal to zero, with smaller amplitudes in the resultant image signal remain unchanged.

55. The method of claim 32, wherein repetitively scanning across the imaging plate with the at least one scanning head comprises:

passing a single scanning head in a straight path across the imaging plate.

56. The method of claim 32, wherein repetitively scanning across the imaging plate with the at least one scanning head comprises:

rotating a multi-head scanner such that successive scanning heads pass in curved paths across the imaging plate.

57. The method of claim 56, wherein the multi-head scanner has three scanning heads.

58. A method of compensating for image artifacts caused by the periodic variances in signal values produced by scanning an exposed imaging plate with an imaging plate scanner having at least one scanning head, comprising:

(a) calculating a correction transfer function corresponding to a repeating pattern of the periodic variances in the signal values;

(b) scanning the at least one scanning head across an imaging plate containing an image thereon, thereby determining an image value at successive locations across the imaging plate for each scan line in the series of scan lines; and (c) applying the correction transfer function to the determined image values at the successive locations along each of the scan lines passing across the imaging plate.

59. The method of claim 58, wherein the periodic variances in signal values produced by an imaging plate scanner comprise periodic speed variances in relative movement between the imaging plate and the imaging plate scanner.

60. The method of claim 58, wherein moving the imaging plate relative to the imaging plate scanner comprises:

moving the imaging plate while the scanner remains positioned at a constant location.

61. The method of claim 58, wherein moving the imaging plate relative to the imaging plate scanner comprises:

moving the scanner while the imaging plate remains positioned at a constant location.

62. The method of claim 58, wherein (b) and (c) are repeated using additional imaging plates having images stored thereon.

63. The method of claim 58, wherein calculating a correction transfer function comprises:

calculating at least one spatial detection filter corresponding to the repeating pattern.

64. The method of claim 63, wherein the at least one spatial detection filter is tuned to a frequency component of the repeating pattern.

65. The method of claim 63, wherein the at least one spatial detection filter is tuned to a summation of a plurality of frequency components of the repeating pattern.

66. The method of claim 58, wherein calculating a correction transfer function comprises:

calculating a subtractive function.

67. The method of claim 66, wherein applying the correction transfer function to the determined image values comprises:

adding correction values to the detected signal measured at successive locations along each scan line, thereby uniformly adjusting image brightness along the scan line.

68. The method of claim 58, wherein calculating a correction transfer function comprises:
calculating a multiplicative function.

69. The method of claim 68, wherein applying the correction transfer function to the determined image values comprises:
multiplying the detected signal measured at successive locations along each scan line by a scale factor derived from the multiplicative function.

70. The method of claim 68, wherein the multiplicative function comprises an inverse of detected signal values representative of each of the scan lines in the series of scan lines.

71. The method of claim 58, further comprising:
(h) clipping large amplitude corrections in a resultant image signal generated by applying the correction transfer function to the determined image values at the successive locations along each of the scan lines passing across the imaging plate in (c).

72. The method of claim 58, further comprising:
(h) applying a modifying transfer function to a resultant image signal generated by applying the correction transfer function to the determined image values at the successive locations along each of the scan lines passing across the imaging plate in (c), wherein the modifying transfer function progressively suppresses larger amplitudes in the resultant image signal to zero, with smaller amplitudes in the resultant image signal remain unchanged.

73. The method of claim 58, wherein scanning the at least one scanning head across the imaging plate comprises:
passing a single scanning head in a straight path across the imaging plate.

74. The method of claim 58, wherein repetitively scanning across the imaging plate with the at least one scanning head comprises:
rotating a multi-head scanner such that successive scanning heads pass in curved paths across the imaging plate.

75. The method of claim 74, wherein the multi-head scanner has three scanning heads.

76. A method of compensating for image artifacts caused by the periodic variances in signal values produced by scanning an exposed imaging plate with an imaging plate scanner having at least one scanning head, comprising:
(a) calculating a correction transfer function corresponding to the repeating pattern in the signal values;
(b) scanning the at least one scanning head across an imaging plate containing an image thereon, thereby determining an image value at successive locations across the imaging plate for each scan line in the series of scan lines; and
(c) varying the speed of relative movement between the imaging plate and the imaging plate scanner in accordance with the correction transfer function.

77. The method of claim 76, wherein varying the speed of relative movement between the imaging plate and the imaging plate scanner in accordance with the correction transfer function comprises:
speeding up the relative motion at those times that the corrective transfer function indicates that the scan lines would otherwise be too close together.

78. The method of claim 76, wherein varying the speed of relative movement between the imaging plate and the imaging plate scanner in accordance with the correction transfer function comprises:
slowing down the relative motion at those times that the corrective transfer function indicates that the scan lines would otherwise be too far apart.

79. A system for compensating for differences in detective gain between a plurality of different scanning heads in a multiple scanning head imaging plate scanner, comprising:
(a) means for scanning each of the scanning heads across an imaging plate thereby determining the detected signal at successive locations across the imaging plate for each of the scanning heads;
(b) means for calculating an inverse relationship to the detected signal at successive locations across the imaging plate for each of the scanning heads;
(c) means for scanning each of the scanning heads across an imaging plate containing an image thereon, thereby determining an image value at the successive locations across the imaging plate for each of the scanning heads; and
(d) means for applying the inverse relationship to the determined image values at the successive locations across the imaging plate for each of the scanning heads.

80. A system for compensating for non-uniformity effects in a rotary scanner, comprising:
(a) means for scanning at least one scanning head across an imaging plate thereby determining the detected signal at successive locations across the imaging plate;
(b) means for calculating an inverse relationship to the detected signal at successive locations across the imaging plate;
(c) means for scanning the at least one scanning head across an imaging plate containing an image thereon, thereby determining an image value at the successive locations across the imaging plate; and
(d) means for applying the inverse relationship to the determined image values at the successive locations across the imaging plate.

81. A system for detecting periodic variances in signal values produced by scanning an exposed imaging plate with an imaging plate scanner having at least one scanning head, comprising:
(a) means for moving the exposed imaging plate relative to the imaging plate scanner while repetitively scanning across the imaging plate with the at least one scanning head such that the at least one scanning head scans across the imaging plate in a series of scan lines which are spaced apart along the length of the blank imaging plate;
(b) means for scanning the at least one scanning head across the imaging plate, thereby measuring a detected signal at successive locations along each scan line in the series of spaced apart scan lines;
(c) means for calculating a signal value representative of each of the scan lines in the series of scan lines; and
(d) means for identifying a repeating pattern in the signal values representative of each scan line in the series of spaced apart scan lines.

82. A system for compensating for image artifacts caused by the periodic variances in signal values produced by scanning an exposed imaging plate with an imaging plate scanner having at least one scanning head, comprising:
(a) means for calculating a correction transfer function corresponding to a repeating pattern of the periodic variances in the signal values;
(b) means for scanning the at least one scanning head across an imaging plate containing an image thereon, thereby determining an image value at successive locations across the imaging plate for each scan line in the series of scan lines; and (c) means for applying the correction transfer function to the determined image values at the successive locations along each of the scan lines passing across the imaging plate.

83. A system for compensating for image artifacts caused by the periodic variances in signal values produced by scanning an exposed imaging plate with an imaging plate scanner having at least one scanning head, comprising:

(a) means for calculating a correction transfer function corresponding to the repeating pattern in the signal values;

(b) means for scanning the at least one scanning head across an imaging plate containing an image thereon, thereby determining an image value at successive locations across the imaging plate for each scan line in the series of scan lines; and (c) means for varying the speed of relative movement between the imaging plate and the imaging plate scanner in accordance with the correction transfer function.

84. A system for compensating for image artifacts produced by variations in the Y-directional speed of an imaging plate with respect to an imaging plate scanner, comprising:

a rotary drive system which moves the imaging plate in an Y-direction relative to the imaging plate scanner;

a control system which varies the speed of movement of the imaging plate in an Y-direction relative to the imaging plate scanner in accordance with a calculated correction transfer function, thereby reducing periodic variations in the Y-directional speed of an imaging plate with respect to an imaging plate scanner.

85. The system of claim 84, wherein the rotary drive mechanism comprises a reference system for determining a rotation angle of the rotary drive mechanism.

86. The system of claim 85, wherein the reference system comprises an encoder wheel.

87. The system of claim 84, wherein the rotary drive system comprises a worm gear.

88. The system of claim 84, wherein the computer system comprises a table of delay times.

89. The system of claim 84, wherein the computer system comprises a timer which determines the timing between successive steps of the rotary drive mechanism.

90. The system of claim 84, wherein the rotary drive mechanism comprises a stepper motor.

* * * * *